United States Patent
Kawashima

(10) Patent No.: US 11,207,056 B2
(45) Date of Patent: Dec. 28, 2021

(54) ULTRASOUND DIAGNOSTIC APPARATUS, METHOD FOR OPERATING ULTRASOUND DIAGNOSTIC APPARATUS, AND COMPUTER-READABLE RECORDING MEDIUM

(71) Applicant: OLYMPUS CORPORATION, Tokyo (JP)

(72) Inventor: Tomonao Kawashima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1081 days.

(21) Appl. No.: 15/810,626

(22) Filed: Nov. 13, 2017

(65) Prior Publication Data

US 2018/0064423 A1 Mar. 8, 2018

Related U.S. Application Data

(63) Continuation of application No. PCT/JP2016/063349, filed on Apr. 28, 2016.

(30) Foreign Application Priority Data

May 13, 2015 (JP) ............................. JP2015-098319

(51) Int. Cl.
*A61B 8/08* (2006.01)
*A61B 8/00* (2006.01)
(Continued)

(52) U.S. Cl.
CPC .............. *A61B 8/5269* (2013.01); *A61B 8/12* (2013.01); *A61B 8/445* (2013.01); *A61B 8/4494* (2013.01);
(Continued)

(58) Field of Classification Search
CPC ....... A61B 8/5269; A61B 8/5292; A61B 8/54; A61B 8/445; A61B 8/4494; A61B 8/461;
(Continued)

(56) References Cited

U.S. PATENT DOCUMENTS 5,891,038 A 4/1999 Seyed-Bolorforosh et al.
2006/0052703 A1* 3/2006 Kumazawa ......... G01S 7/52052
600/447
(Continued)

FOREIGN PATENT DOCUMENTS

JP 5433097 B2 3/2014
WO 2012063928 A1 5/2012
(Continued)

OTHER PUBLICATIONS

Gammex. 404GS LE Precision Small Parts Grey Scale Phantom: User's Guide [online]. Sep. 20, 2012 [retrieved on Dec. 12, 2020]. Retrieved from the Internet: <URL: https://biomedequip.com/image/data/PDF/006288-00-09_404_GS_LE.pdf>. (Year: 2012).*
(Continued)

*Primary Examiner* — Joanne M Hoffman
*Assistant Examiner* — Alexei Bykhovski
(74) *Attorney, Agent, or Firm* — Scully, Scott, Murphy & Presser, P.C.

(57) ABSTRACT

An ultrasound diagnostic apparatus generates an ultrasound image based on an ultrasound signal acquired by an ultrasound probe having an ultrasound transducer. The ultrasound transducer transmits an ultrasound wave to an observation target and receives the ultrasound wave reflected from the observation target. The apparatus includes: an analysis unit configured to generate analysis data based on the ultrasound signal received from the observation target; and a correction unit configured to correct the analysis data using correction data based on first reference data and
(Continued)

second reference data, the first reference data being obtained from an ultrasound signal received from a reference reflector by using the ultrasound transducer or another ultrasound transducer of a same type as that of the ultrasound transducer, the second reference data being obtained from the ultrasound signal received from the reference reflector by using still another ultrasound transducer of different type from that of the ultrasound transducer.

18 Claims, 10 Drawing Sheets

(51) Int. Cl.
*A61B 8/12* (2006.01)
*G01S 7/52* (2006.01)
*G01S 15/89* (2006.01)

(52) U.S. Cl.
CPC ............ *A61B 8/461* (2013.01); *A61B 8/5207* (2013.01); *A61B 8/5292* (2013.01); *A61B 8/54* (2013.01); *G01S 7/52033* (2013.01); *G01S 7/52036* (2013.01); *G01S 7/52071* (2013.01); *G01S 7/52074* (2013.01); *G01S 15/892* (2013.01); *G01S 15/8977* (2013.01); *A61B 8/585* (2013.01)

(58) Field of Classification Search
CPC ......... A61B 8/5207; A61B 8/12; A61B 8/585; G01S 7/52074; G01S 7/52033; G01S 7/52036; G01S 7/52071; G01S 15/8977; G01S 15/892
USPC .................................................. 600/437, 443
See application file for complete search history.

(56) References Cited

U.S. PATENT DOCUMENTS

| | | | |
|---|---|---|---|
| 2013/0035594 A1* | 2/2013 | Eda | G01S 7/52046 600/442 |
| 2016/0074008 A1 | 3/2016 | Eda | |
| 2020/0029939 A1* | 1/2020 | Kawashima | A61B 8/585 |

FOREIGN PATENT DOCUMENTS

| WO | 2015/008534 A1 | 1/2015 | |
|---|---|---|---|
| WO | WO-2015008534 A1 * | 1/2015 | ............ A61B 8/4477 |

OTHER PUBLICATIONS

International Search Report dated Jun. 7, 2016 issued in PCT/JP2016/063349.
Supplementary Extended European Search Report dated Jan. 17, 2019 received in EP 16792581.7.

* cited by examiner

ULTRASOUND DIAGNOSTIC APPARATUS, METHOD FOR OPERATING ULTRASOUND DIAGNOSTIC APPARATUS, AND COMPUTER-READABLE RECORDING MEDIUM

CROSS REFERENCES TO RELATED APPLICATIONS

This application is a continuation of PCT international application Ser. No. PCT/JP2016/063349, filed on Apr. 28, 2016 which designates the United States, incorporated herein by reference, and which claims the benefit of priority from Japanese Patent Application No. 2015-098319, filed on May 13, 2015, incorporated herein by reference.

BACKGROUND

1. Technical Field

The disclosure relates to an ultrasound diagnostic apparatus for observing tissue of an observation target using an ultrasound wave. The disclosure also relates to a method for operating the ultrasound diagnostic apparatus, and a computer-readable recording medium.

2. Related Art

In the related art, as a technique of observing tissue characteristics of an observation target such as a subject by using an ultrasound wave, there is known a technique of visualizing feature of a frequency spectrum of a received ultrasound signal as an image (for example, refer to JP 5433097 B2). In the technique, the feature of the frequency spectrum is extracted as an analysis value representing the tissue characteristics of the observation target, and after that, a feature image where the corresponding visual information is applied to the feature is generated to be displayed. An operator such as a doctor diagnoses the tissue characteristics of the subject by viewing the displayed feature image.

SUMMARY

In some embodiments, provided is an ultrasound diagnostic apparatus for generating an ultrasound image based on an ultrasound signal acquired by an ultrasound probe having an ultrasound transducer, the ultrasound transducer being configured to transmit an ultrasound wave to an observation target and to receive the ultrasound wave reflected from the observation target. The ultrasound diagnostic apparatus includes: an analysis unit configured to generate analysis data based on the ultrasound signal received from the observation target; and a correction unit configured to correct the analysis data by using correction data based on first reference data and second reference data, the first reference data being obtained from an ultrasound signal received from a reference reflector by using the ultrasound transducer or another ultrasound transducer of a same type as that of the ultrasound transducer, the second reference data being obtained from the ultrasound signal received from the reference reflector by using still another ultrasound transducer of different type from that of the ultrasound transducer.

In some embodiments, provided is a method for operating an ultrasound diagnostic apparatus for generating an ultrasound image based on an ultrasound signal acquired by an ultrasound probe having an ultrasound transducer, the ultrasound transducer being configured to transmit an ultrasound wave to an observation target and to receive the ultrasound wave reflected from the observation target. The method includes: generating, by an analysis unit, analysis data based on the ultrasound signal received from the observation target; and correcting, by a correction unit, the analysis data by using correction data based on first reference data and second reference data, the first reference data being obtained from an ultrasound signal received from a reference reflector by using the ultrasound transducer or another ultrasound transducer of a same type as that of the ultrasound transducer, the second reference data being obtained from the ultrasound signal received from the reference reflector by using still another ultrasound transducer of different type from that of the ultrasound transducer.

In some embodiments, provided is a non-transitory computer-readable recording medium with an executable program stored thereon for operating an ultrasound diagnostic apparatus, the ultrasound diagnostic apparatus being configured to generate an ultrasound image based on an ultrasound signal acquired by an ultrasound probe having an ultrasound transducer, the ultrasound transducer being configured to transmit an ultrasound wave to an observation target and to receive the ultrasound wave reflected from the observation target. The program causes the ultrasound diagnostic apparatus to execute: generating, by an analysis unit, analysis data based on the ultrasound signal received from the observation target; and correcting, by a correction unit, the analysis data by using correction data based on first reference data and second reference data, the first reference data being obtained from an ultrasound signal received from a reference reflector by using the ultrasound transducer or another ultrasound transducer of a same type as that of the ultrasound transducer, the second reference data being obtained from the ultrasound signal received from the reference reflector by using still another ultrasound transducer of different type from that of the ultrasound transducer.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, modes for carrying out the present invention (hereinafter, referred to as embodiment(s)) will be described with reference to the attached drawings.

Embodiments

Figure 1:
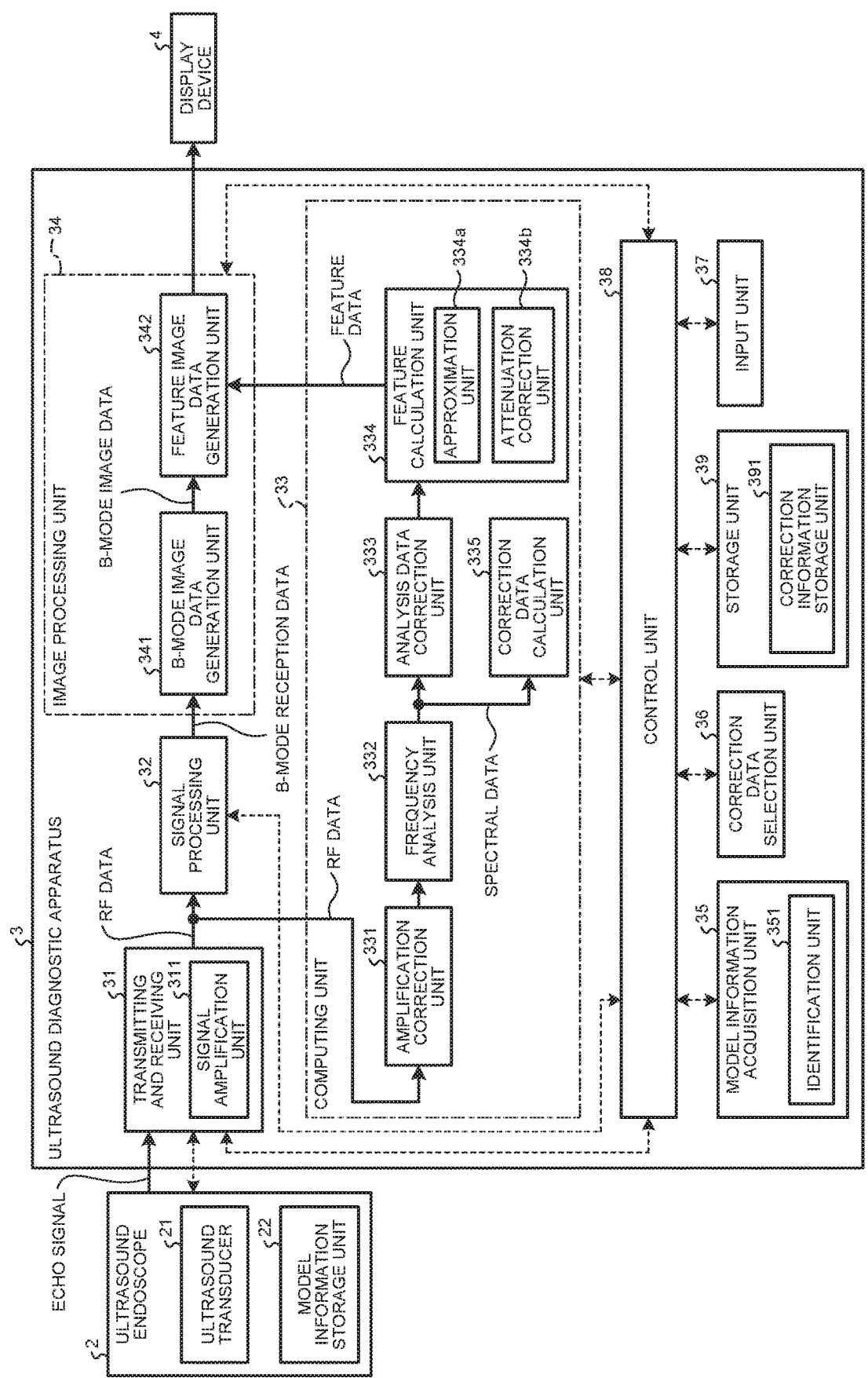
FIG. 1 is a block diagram illustrating a configuration of an ultrasound diagnostic system including an ultrasound diagnostic apparatus according to an embodiment of the present invention.

FIG. 1 is a block diagram illustrating a configuration of an ultrasound diagnostic system 1 including an ultrasound diagnostic apparatus 3 according to an embodiment of the present invention. The ultrasound diagnostic system 1 illustrated in FIG. 1 is configured to include an ultrasound endoscope 2 (ultrasound probe) which transmits an ultrasound wave to a subject as an observation target and receives the ultrasound wave reflected from the subject, an ultrasound diagnostic apparatus 3 which generates an ultrasound image based on an ultrasound signal acquired by the ultrasound endoscope 2, and a display device 4 which displays the ultrasound image generated by the ultrasound diagnostic apparatus 3. The ultrasound diagnostic apparatus 3 can be connected with one ultrasound endoscope 2 or can be simultaneously connected with a plurality of ultrasound endoscopes 2. In FIG. 1, solid line arrows indicate transfer of electric signals associated with images, and broken line arrows indicate transfer of electrical signals associated with control.

The ultrasound endoscope 2 is configured to include, at the distal end thereof, an ultrasound transducer 21 which converts an electric pulse signal received from the ultrasound diagnostic apparatus 3 to an ultrasound pulse (acoustic pulse) to irradiate the subject with the ultrasound pulse and converts an ultrasound echo reflected from the subject to an electric echo signal represented by a voltage change to output the electric echo signal and a model information storage unit 22 which stores model information of the ultrasound endoscope 2. The ultrasound endoscope 2 includes a standard ultrasound endoscope, a correction ultrasound endoscope, and a biological observation ultrasound endoscope described later.

The model information stored in the model information storage unit 22 includes information on at least a model of the ultrasound transducer 21 or a machine body of the ultrasound endoscope 2.

The ultrasound endoscope 2 is generally configured to include an imaging optical system and an imaging device. The ultrasound endoscope can be inserted into a digestive tract (esophagus, stomach, duodenum, colon, or the like) or a respiratory organ (trachea, bronchial tube, or the like) of the subject and can capture an image of the digestive tract, the respiratory organ, or a peripheral organ (pancreas, gall bladder, bile duct, biliary tract, lymph node, mediastinal organ, blood vessel, or the like). The ultrasound endoscope 2 is configured to include a light guide which guides illumination light with which the subject is illuminated at the time of imaging. The light guide is configured so that the distal end thereof reaches the distal end of the insertion portion of the ultrasound endoscope 2 inserted into the subject, and the base end thereof is connected to a light source device which generates illumination light.

The ultrasound diagnostic apparatus 3 is configured to include a transmitting and receiving unit 31 which is electrically connected to the ultrasound endoscope 2 to transmit a transmission signal (pulse signal) configured with a high voltage pulse to the ultrasound transducer 21 based on a predetermined wave form and a transmission timing and to receive the echo signal as an electric reception signal from the ultrasound transducer 21 to generate and output data of a digital radio frequency (RF) signal (hereinafter, referred to as RF data), a signal processing unit 32 which generates digital B-mode reception data based on the RF data received from the transmitting and receiving unit 31, a computing unit 33 which performs predetermined calculation on the RF data received from the transmitting and receiving unit 31, an image processing unit 34 which generates various types of image data, a model information acquisition unit 35 which acquires the model information of the ultrasound endoscope 2 connected to the ultrasound diagnostic apparatus 3 to identify the connected ultrasound endoscope 2, a correction data selection unit 36 which selects correction data of the ultrasound endoscope 2 according to a result of identification performed by the model information acquisition unit 35, an input unit 37 which is configured by using a user interface such as a keyboard, a mouse, or a touch panel and receives various types of information as an input, a control unit 38 which controls the overall ultrasound diagnostic system 1, and a storage unit 39 which stores various types of information required for operations of the ultrasound diagnostic apparatus 3.

Figure 2:
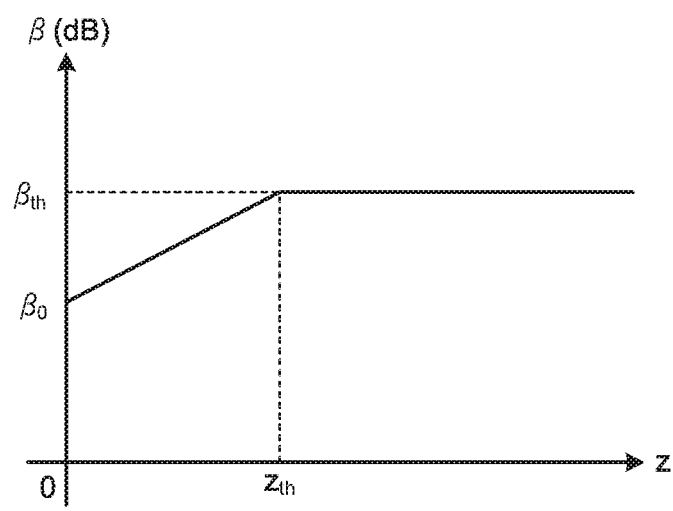
FIG. 2 is a graph illustrating a relationship between a reception depth and an amplification factor in an amplification process performed by a signal amplification unit of the ultrasound diagnostic apparatus according to the embodiment of the present invention.

The transmitting and receiving unit 31 is configured to include a signal amplification unit 311 which amplifies the echo signal. The signal amplification unit 311 performs sensitivity time control (STC) correction by which an echo signal having a lager reception depth is amplified with a higher amplification factor. FIG. 2 is a graph illustrating a relationship between the reception depth and the amplification factor in an amplification process performed by the signal amplification unit 311. The reception depth z illustrated in FIG. 2 is an amount calculated based on a time elapsed from a reception start time point for an ultrasound wave. As illustrated in FIG. 2, if the reception depth z is smaller than a threshold value $z_{th}$, the amplification factor β (dB) is linearly increased from $β_0$ to $β_{th}$ ($>β_0$) in accordance with the increase of the reception depth z. If the reception depth z is equal to or larger than the threshold value $z_{th}$, the amplification factor β (dB) has a constant value $β_{th}$. The threshold value $z_{th}$ is a value in a case where the ultrasound signal received from the observation target is almost attenuated and, thus, noise is dominant. More generally, if the reception depth z is smaller than the threshold value $z_{th}$, the amplification factor β may be monotonously increased in accordance with the increase of the reception depth z. The relationship illustrated in FIG. 2 is stored in the storage unit 39 in advance.

The transmitting and receiving unit 31 performs a process such as filtering on the echo signal amplified by the signal amplification unit 311, generates time-domain RF data by performing sampling at an appropriate sampling frequency (for example, 50 MHz) and discretization (so-called an A/D conversion process), and outputs the RF data to the signal processing unit 32 and the computing unit 33. In a case where the ultrasound endoscope 2 is configured such that the ultrasound transducer 21 having a plurality of elements in an array shape is allowed to electronically scan, the transmitting and receiving unit 31 has a multi-channel circuit for beam combination according to a plurality of elements.

The frequency band of a pulse signal transmitted by the transmitting and receiving unit 31 is set to be a wide band which almost covers a linear response frequency band at the time when the ultrasound transducer 21 performs electric-acoustic conversion of the pulse signal to an ultrasound pulse. The frequency band of various processes for the echo signal in the signal amplification unit 311 is set to be a wide band which almost covers a linear response frequency band at the time when the ultrasound transducer 21 performs acoustic-electric conversion of an ultrasound echo to an echo signal. Therefore, at the time of performing a frequency spectrum approximation process described later, it is possible to perform approximation at a good accuracy.

The transmitting and receiving unit 31 has a function of transmitting various types of control signals output by the control unit 38 to the ultrasound endoscope 2 and a function of receiving various types of information including ID for identification from the model information storage unit 22 of the ultrasound endoscope 2 and transmitting various types of information to the control unit 38.

Figure 3:
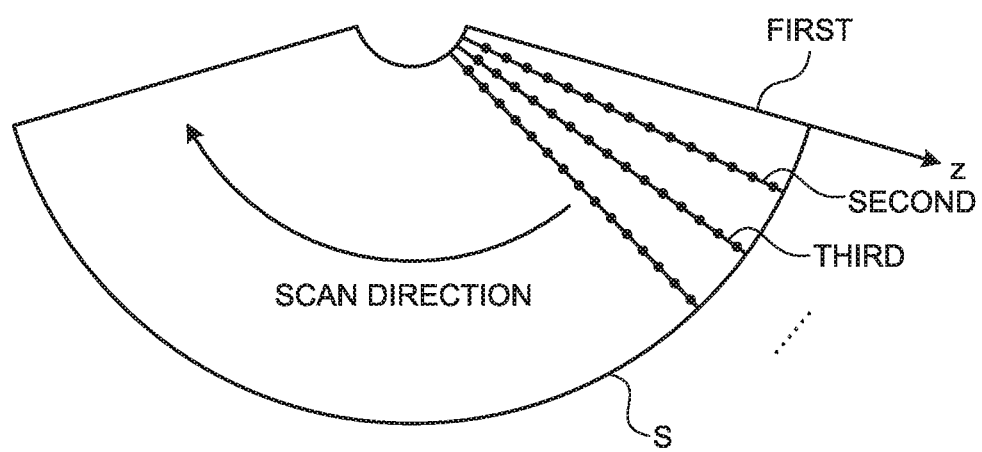
FIG. 3 is a schematic diagram illustrating a scan region of an ultrasound transducer and a B-mode reception data.

The signal processing unit 32 performs well-known processes such as band pass filtering, envelope detection, and logarithmic conversion on the RF data to generate digital B-mode reception data. In the logarithmic conversion, the RF data is expressed as a decibel value by taking common logarithm of an amount obtained by dividing the RF data by a reference voltage $V_c$. In the B-mode reception data, an amplitude or intensity of the reception signal representing the intensity of reflection of the ultrasound pulse is aligned along the transmission/reception direction (depth direction) of the ultrasound pulse. FIG. 3 is a schematic diagram illustrating a scan region (hereinafter, sometimes simply referred to as a scan region) of the ultrasound transducer 21 and the B-mode reception data. As illustrated in FIG. 3, the scan region S has a fan shape. In FIG. 3, a path (sound ray) of reciprocation of the ultrasound wave is indicated by a straight line, and the B-mode reception data is represented as points aligned on each sound ray. In FIG. 3, for the convenience of the later description, the sound rays are denoted by numbers such as 1, 2, 3, . . . in the order from the scan start (right side of FIG. 3). The first sound ray is defined as $SR_1$, the second sound ray is defined as $SR_2$, the third sound ray is defined as $SR_3$, . . . , and the k-th sound ray is defined as $SR_k$. FIG. 3 corresponds to the case where the ultrasound transducer 21 is a convex vibrator. In FIG. 3, the reception depth of the B-mode reception data is denoted by z. In a case where the ultrasound pulse irradiated from the surface of the ultrasound transducer 21 is reflected from a reflector at the reception depth z and is returned as an ultrasound echo to the ultrasound transducer 21, the relationship between the round-trip distance L and reception depth z is z=L/2. The signal processing unit 32 outputs the generated B-mode reception data to a B-mode image data generation unit 341 of the image processing unit 34. The signal processing unit 32 is embodied by using a CPU (Central Processing Unit), various types of calculation circuits, or the like.

The computing unit 33 is configured to include an amplification correction unit 331 which performs amplification correction on the RF data generated by the transmitting and receiving unit 31 at a constant amplification factor β irrespective of the reception depth, a frequency analysis unit 332 (analysis unit) which calculates spectral data by performing frequency analysis by performing fast fourier transform (FFT) on the RF data on which the amplification correction is performed, an analysis data correction unit 333 (correction unit) which performs correction on the spectral data calculated by the frequency analysis unit 332, a feature calculation unit 334 which calculates feature of the frequency spectrum, and a correction data calculation unit 335 which calculates correction data used for the correction of the spectral data performed by the analysis data correction unit 333. The computing unit 33 is embodied by using a central processing unit (CPU), various types of calculation circuits, or the like.

Figure 4:
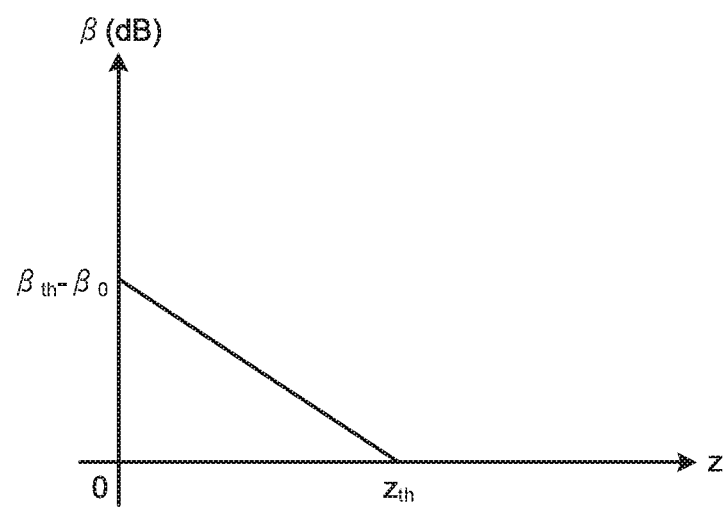
FIG. 4 is a graph illustrating a relationship between a reception depth and an amplification factor in an amplification correction process performed by an amplification correction unit of the ultrasound diagnostic apparatus according to the embodiment of the present invention.

FIG. 4 is a graph illustrating a relationship between the reception depth and the amplification factor in the amplification correction process performed by the amplification correction unit 331. As illustrated in FIG. 4, the amplification factor β (dB) in the amplification correction process performed by the amplification correction unit 331 takes a maximum value $β_{th}$–$β_0$ when the reception depth z is zero. The amplification factor is linearly decreased as the reception depth z goes from zero to the threshold value $z_{th}$. The amplification factor is zero when the reception depth z is equal to the threshold value $z_{th}$ or more. The amplification correction unit 331 performs the amplification correction on the RF data using the amplification factor defined in this manner, and thus, the influence of the STC correction in the signal processing unit 32 can be canceled, so that a signal with the constant amplification factor $β_{th}$ can be output. Needless to say, the relationship between the reception depth z and the amplification factor β in the amplification correction performed by the amplification correction unit 331 is different depending on the relationship between the reception depth and the amplification factor in the signal processing unit 32.

The reason why the amplification correction is performed will be described. The STC correction is a correction process of removing the influence of the attenuation from the amplitude of the analog signal wave form by amplifying the amplitude of the analog signal wave form uniformly over the entire frequency band and with the amplification factor monotonously increased with respect to the depth. For this reason, in the case of generating the B-mode image displayed by converting the amplitude of the echo signal to the luminance, and in the case of scanning a uniform tissue, when the STC correction is performed, the luminance value becomes constant irrespective of the depth. That is, the effect that the influence of the attenuation is removed from the luminance value of the B-mode image is obtained.

On the other hand, like the embodiment, in the case of using the result obtained by calculating and analyzing the frequency spectrum of the ultrasound wave, even though the STC correction is performed, the influence of the attenuation involved with the propagation of the ultrasound wave may not be accurately removed. The reason is as follows. In general, the attenuation amount is different according to the frequency (refer to an attenuation amount 2ζzf described later). However, the amplification factor of the STC correction is changed according to the distance and has no frequency dependency, and the change of the spectrum caused by the attenuation cannot be corrected.

Therefore, in the embodiment, in order to remove the influence of the STC correction from the RF data, the correction for the amplification factor illustrated in FIG. 4 is performed by the amplification correction unit 331

The frequency analysis unit 332 re-samples the RF data (line data) of each sound ray on which the amplification correction unit 331 performs the amplification correction at a predetermined time interval to generate sample data. The frequency analysis unit 332 calculates the frequency spectrum (analysis data) at multiple sites (data positions) on the RF data by applying the FFT process to the sample data group. Herein, the "frequency spectrum" denotes a "frequency distribution of intensity at a certain reception depth z" obtained by applying the FFT process to the sample data group. Herein, the "intensity" denotes, for example, any one of parameters such as a voltage of an echo signal, a power of an echo signal, a sound pressure of an ultrasound echo, and acoustic energy of an ultrasound echo, amplitudes or time integral values of the parameters, and a combination thereof.

In the embodiment, the voltage of the echo signal is employed as an intensity, and the frequency analysis unit 332 generates data (hereinafter, sometimes referred to as spectral data) of a frequency spectrum based on a frequency component V(f,L) of a voltage amplitude. f is a frequency. The frequency analysis unit 332 generates the spectral data F(f,L) given by the following Formula (1) by dividing the frequency component V(f,L) of the voltage amplitude by a reference voltage $V_c$ and applying a logarithm conversion process of taking common logarithm (log) to express in unit of a decibel, and multiplying an appropriate positive constant A.

$$F(f,L)=A\cdot\log\{V(f,L)/V_c\} \quad (1)$$

Herein, log is common logarithm (hereinafter, it is the same).

Hereinafter, a method of obtaining the frequency component V(f,L) of the voltage amplitude by the frequency analysis in the frequency analysis unit 332 will be described. In general, in a case where the observation target is a biological tissue, the frequency spectrum of the echo signal exhibits different tendency according to the properties of the biological tissue on which the ultrasound wave is scanned. This is because the frequency spectrum has a correlation with a size, a number density, acoustic impedance, or the like of scatterers scattering the ultrasound wave. Herein, the "properties of the biological tissue" are properties of, for example, malignant tumor (cancer), benign tumor, endocrine tumor, mucinous tumors, normal tissue, cyst, vessel, or the like.

Figure 5:
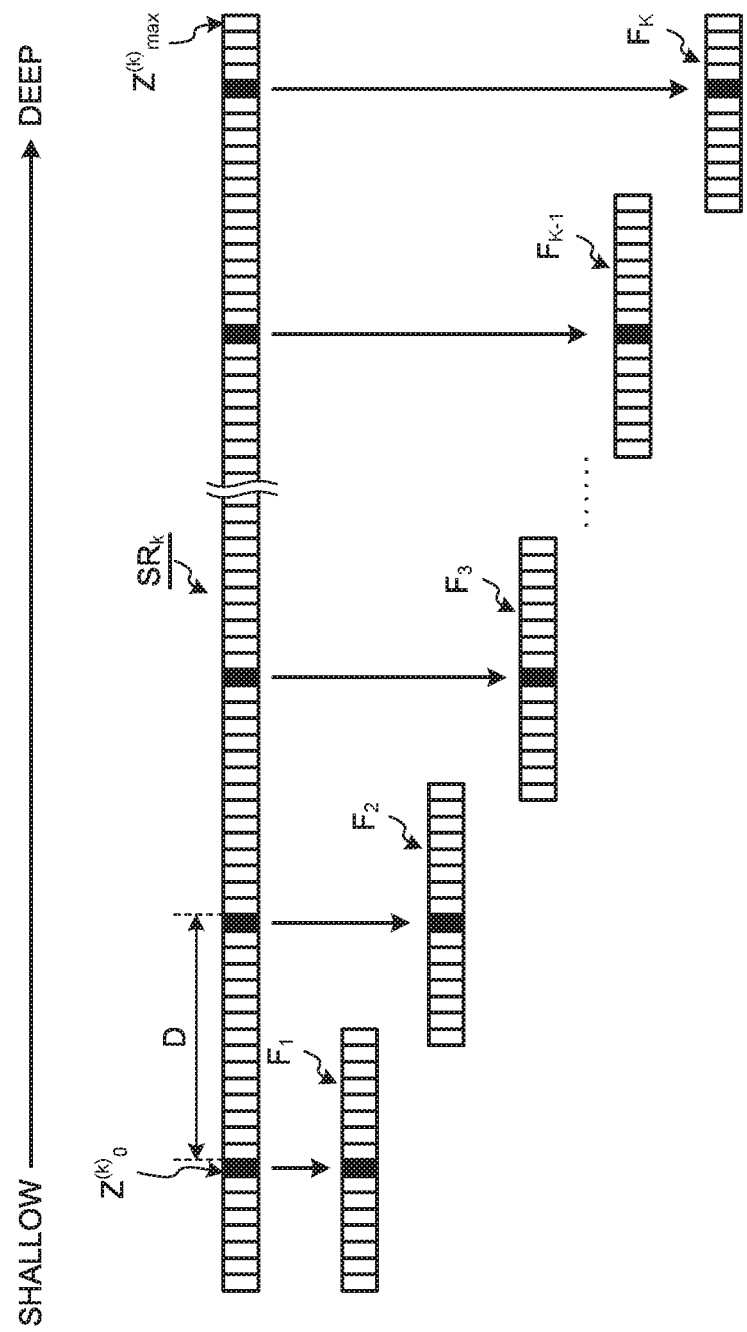
FIG. 5 is a schematic diagram illustrating data arrangement in one sound ray of an ultrasound signal.

FIG. 5 is a schematic diagram illustrating data arrangement in one sound ray $SR_k$ of an ultrasound signal. A white or black rectangle in the sound ray $SR_k$ denotes data at one sample point. In the sound ray $SR_k$, data located at a position closer to the right side are sample data from a deeper site in the case of measuring the depth along the sound ray $SR_k$ from the ultrasound transducer 21 (refer to arrows in FIG. 5). As described above, the sound ray $SR_k$ is the sample data obtained by the frequency analysis unit 332 sampling the RF data which are sampled and discretized from the echo signal by the A/D conversion process in the transmitting and receiving unit 31. In FIG. 5, illustrated is the case where the eighth data position of the sound ray $SR_k$ with the number k is set as an initial value $Z^{(k)}_0$ in the direction of the reception depth z. However, the position of the initial value may be arbitrarily set. The result of calculation of the frequency analysis unit 332 is a complex number and is stored in the storage unit 39.

A data group $F_j$ (j=1, 2, ... K) illustrated in FIG. 5 is the sample data group as an object of the FFT process. In general, in order to perform the FFT process, the sample data group needs to have the number of data that is two to the powers. In this sense, the sample data group $F_j$ (j=1, 2, ..., K−1) is a normal data group of which the number of data is 16 (=$2^4$), and the sample data group $F_K$ is an upper limit data group because the number of data is 12. At the time of performing the FFT process on the upper limit data group, by inserting zero data to cover shortfall, the process of generating a normal sample data group is performed. This point will be described in detail when the process of the frequency analysis unit 332 is described (refer to FIG. 12). Next, as described above, the frequency analysis unit 332 performs the FFT process, calculates the frequency component V(f,L) of the voltage amplitude, calculates the spectral data F(f,L) based on the above-described Formula (1), and outputs the spectral data to the analysis data correction unit 333 and the correction data calculation unit 335.

The analysis data correction unit 333 corrects the spectral data by adding the correction data to a plurality of spectral data (analysis data) calculated by the frequency analysis unit 332. Specifically, the analysis data correction unit 333 corrects the spectral data by using the correction data calculated based on two reference data of theoretical data (first reference data) for the same model which are obtained based on an ultrasound signal received from a reference phantom (reference reflector) by using a correction ultrasound endoscope including the ultrasound transducer 21 or an ultrasound transducer 21 which is the same model as the ultrasound transducer 21 and theoretical data (second reference data) which are obtained based on the ultrasound signal received from the reference phantom by using a standard ultrasound endoscope including a specific standard ultrasound transducer and become a reference of the analysis data correction. A method of calculating the correction data will be described later.

Figure 6:
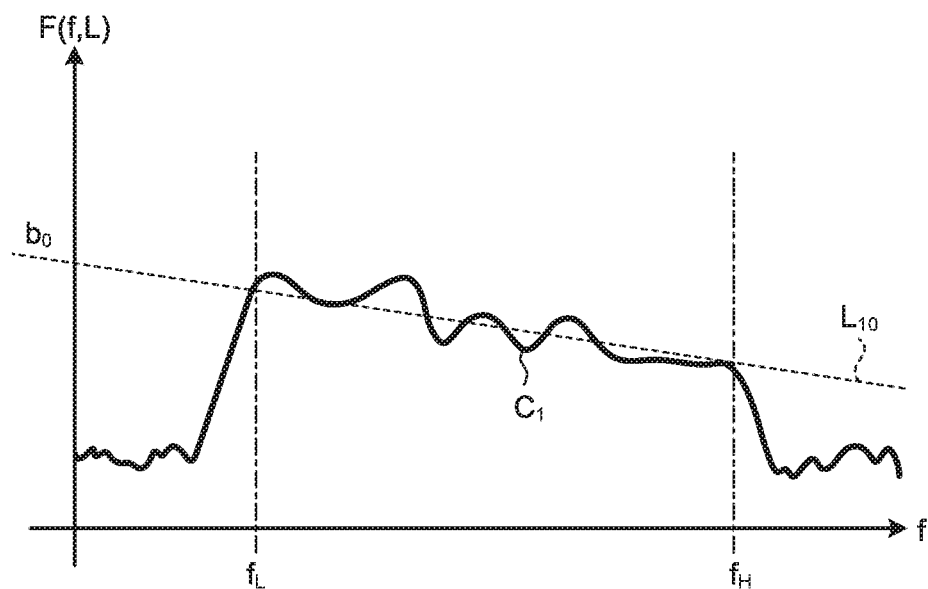
FIG. 6 is a graph illustrating an example of spectral data corrected by the analysis data correction unit of the ultrasound diagnostic apparatus according to the embodiment of the present invention.

FIG. 6 is a graph illustrating an example of spectral data corrected by the analysis data correction unit 333. In FIG. 6, the horizontal axis is a frequency f. In FIG. 6, the vertical axis is the spectral data F(f,L) given by the above Formula (1). A straight line $L_{10}$ illustrated in FIG. 6 will be described later. In the embodiment, a curve and a straight line are configured with sets of discrete points.

In the spectral data $C_1$ illustrated in FIG. 6, the lower limit frequency $f_L$ and the upper limit frequency $f_H$ of the frequency band used in the calculation hereinafter are parameters determined based on the frequency band of the ultrasound transducer 21, the frequency band of the pulse signal transmitted by the transmitting and receiving unit 31, or the like. Hereinafter, in FIG. 6, the frequency band determined based on the lower limit frequency $f_L$ and the upper limit frequency $f_H$ is referred to as a "frequency band U".

The feature calculation unit 334 is configured to include an approximation unit 334a which calculates feature (hereinafter, referred to as uncorrected feature) of the spectral data before the performing of the attenuation correction process by approximating a plurality of spectral data output from the analysis data correction unit 333 by using a straight line and an attenuation correction unit 334b which calculates feature by performing attenuation correction on the uncorrected feature calculated by the approximation unit 334a.

The approximation unit 334a calculates the uncorrected feature specifying an approximate linear equation by approximating the spectral data by using a linear equation (regression straight line) by performing a regression analysis of the spectral data in a predetermined frequency band. For example, in a case where the spectral data is in the $C_1$ state illustrated in FIG. 6 (the case of the spectral data corrected by the analysis data correction unit 333), the approximation unit 334a obtains a regression straight line $L_{10}$ by approximating the spectral data $C_1$ by using the linear equation by performing the regression analysis in the frequency band U. Next, the approximation unit 334a calculates a slope $a_0$ and an intercept $b_0$ of the regression straight line $L_{10}$ and a mid-band fit $c_0 = a_0 f_M + b_0$ which is a value of a center frequency (i.e., "mid-band") $f_M = (f_L + f_H)/2$ of the frequency band U on the regression straight line as the uncorrected feature.

Among the three uncorrected feature, the slope $a_0$ has a correlation with the size of the scatterer for the ultrasound wave. In general, it is considered that a large scatterer has a smaller slope. The intercept $b_0$ has a correlation with the size of the scatterer, a difference in acoustic impedance, the number density (concentration) of scatterers, and the like. Specifically, it is considered that the intercept $b_0$ has a larger value as the scatterer is larger, the intercept has a larger value as the difference in acoustic impedance is larger, and the intercept has a larger value as the number density of scatters is larger. The mid-band fit $c_0$ is an indirect parameter derived from the slope $a_0$ and the intercept $b_0$ and provides an intensity of the spectrum which is to be placed at the center of the effective frequency band. For this reason, it is considered that the mid-band fit $c_0$ has a certain degree of correlation with luminance of the B-mode image as well as the size of the scatterer, the difference in acoustic impedance, and the number density of scatterers. Subsequently, the approximation unit 334a outputs the uncorrected feature $a_0$, $b_0$, and $c_0$ to the attenuation correction unit 334b. The approximation unit 334a may be allowed to approximate the spectral data by using a second-order or higher order polynomial equation in the regression analysis.

The correction performed by the attenuation correction unit 334b will be described. Herein, the attenuation amount of the spectral data F(f,L) by the attenuation of ultrasound wave (strictly speaking, sound pressure amplitude P(f,L)) will be described. In general, it has been known empirically that, in a case where a medium is uniform, a sound pressure amplitude P(f,L) at a frequency f of an ultrasound wave from a reflector located in a round-trip distance L is given as the following Formula by using a positive constant $\mu$.

$$P(f,L) = P(f,0) \cdot \exp(-\mu f L) \quad (2)$$

Since $\mu > 0$, the Formula (2) denotes that the sound pressure amplitude P(f,L) is attenuated exponentially as the frequency f and the round-trip distance L are increased.

On the other hand, when the attenuation amount of the sound pressure amplitude in the round-trip distance interval $(L, L+\Delta L)$ at the frequency f is denoted by Loss(f,L) [dB], the attenuation amount is defined as follows.

$$\text{Loss}(f,L) = A \cdot \log\{P(f,L)/P(f,L+\Delta L)\} = A \cdot \log P(f,L) - A \cdot \log P(f, L+\Delta L) \quad (3)$$

Herein, a constant A in the right-hand side is the same as the constant A in Formula (1). A ratio per unit distance and per unit frequency is defined as an "attenuation rate" and is denoted by $\zeta$. If the definition is applied to Formula (2), the attenuation rate $\zeta$ is given by the following Formula.

$$\zeta = (\partial/\partial f)\text{Lim}\{\text{Loss}(f,L)/\Delta L\} = (\partial/\partial f)\{-A(\partial/\partial L)\log P(f,L)\} = -A(\partial^2/\partial f \partial L)\log P(f,L) \quad (4)$$

Herein, $\text{Lim}\{\text{Loss}(f,L)/\Delta L\}$ denotes a limit of the function $\text{Loss}(f,L)/\Delta L$ as $\Delta L \to 0$.

The relationship between the constant $\mu$ and the attenuation rate $\zeta$ is as follows. By substituting Formula (2) into the P(f,L) in Formula (4), the attenuation rate $\zeta$ is obtained as follows.

$$\zeta = -A(\partial^2/\partial f \partial L)[\log\{P(f,0) \cdot \exp(-\mu f L)\}] = -A(\partial^2/\partial f \partial L)\{\log P(f,0) - \mu f L \log e\} = (\log e) A \mu \quad (5)$$

Herein, e is the base of natural logarithm. It can be understood from Formula (1) that the attenuation rate $\zeta$ is also a positive constant.

When a sensitivity of the ultrasound transducer 21 is denoted by $\gamma(f)$ as a function of the frequency f, the amplitude component V(f,L) obtained after the applying of the FFT process to the RF data is given by the following Formula (6).

$$V(f,L) = \gamma(f) \cdot P(f,L) \quad (6)$$

By substituting Formula (2) into the P(f,L) in Formula (6), the following equation is obtained.

$$V(f,L) = \gamma(f) \cdot P(f,0) \cdot \exp(-\mu f L) = V(f,0) \cdot \exp(-\mu f L) \quad (7)$$

By substituting Formula (7) into Formula (1), the following equation is obtained.

$$F(f,L) = A \cdot \log\{V(f,0) \cdot \exp(-\mu f L)/V_c\} = A \log \cdot \exp(-\mu f L) + A \log\{V(f,0)/V_c\} = -(\log e) A \mu f L + F(f,0) \quad (8)$$

By substituting Formula (5) into the right-hand side of Formula (8), the following equation is derived.

$$F(f,L) - F(f,0) = -\zeta f L \quad (9)$$

The later-described Formula (14) is obtained from Formula (9). In a case where the observation target is a living body, a specific value of the attenuation rate $\zeta$ is determined according to a portion of the living body. The unit of the attenuation rate $\zeta$ is [dB/cm/MHz], for example. In the embodiment, a configuration where the value of the attenuation rate $\zeta$ can be changed according to an input from the input unit 37 may also be provided.

The attenuation amount of the spectral data F(f,L) caused by the attenuation while the ultrasound wave reciprocates the reception depth z is $2\zeta z f$ from Formula (9). Since the spectral data F(f,L) of each frequency f is attenuated by $2\zeta z f$, when the horizontal axis denotes the frequency f, the curve of the spectral data is uniformly descending toward the right side. The attenuation amount of the slope $a_0$ is $2\zeta z$ [dB/MHz]. That is, the attenuation correction amount of the slope $a_0$ is $2\zeta z$, and the attenuation correction can be performed by adding the attenuation correction amount to the uncorrected feature $a_0$. Therefore, the after-attenuation-correction slope a is obtained by the following Formula.

$$a = a_0 + 2\zeta z \quad (10)$$

Since it is considered that the intercept $b_0$ is a spectral component at the frequency f=0, the attenuation amount of the intercept $b_0$ is $2\zeta z \times 0 = 0$ [dB]. That is, since the intercept $b_0$ is not attenuated, the after-attenuation-correction intercept b is obtained by the following Formula.

$$b = b_0 \quad (11)$$

Finally, the before-attenuation-correction mid-band fit $c_0$ is defined to be $c_0 = a_0 f_M + b_0$, and the after-attenuation-correction mid-band fit c is defined to be $c = a f_M + b$. Therefore, the attenuation correction amount of the mid-band fit $c_0$ is $c-c_0=(a-a_0) f_M$, and the after-attenuation-correction mid-band fit c is obtained by the following Formula.

$$c=c_0+(a-a_0)f_M=c_0+(a_0+2\zeta z-a_0)f_M=c_0+2\zeta z f_M \quad (12)$$

Figure 7:
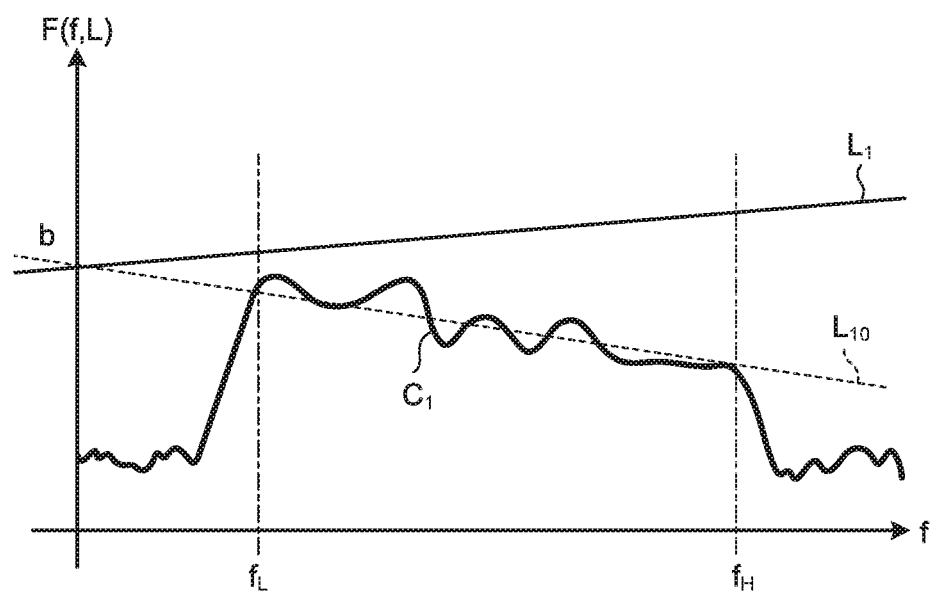
FIG. 7 is a graph illustrating a straight line having, as parameters, feature calculated by an attenuation correction unit of the ultrasound diagnostic apparatus according to the embodiment of the present invention.

FIG. 7 is a graph illustrating a straight line having, as parameters, the feature a, b, and c calculated by the attenuation correction unit 334b. Formula for the straight line $L_1$ is expressed as follows.

$$F(f,L)=af+b=(a_0+2\zeta z)f+b_0 \quad (13)$$

As clarified from Formula (13), in comparison with the before-attenuation-correction straight line $L_{10}$, straight line $L_1$ has a large slope ($a>a_0$) and has the same intercept ($b=b_0$). Subsequently, the feature calculation unit 334 outputs the attenuation-corrected feature a, b, and c to the image processing unit 34.

The correction data calculation unit 335 calculates the correction data based on the spectral data F(f,L) generated under a certain appropriate condition by the frequency analysis unit 332. Details of the correction data will be described later.

The image processing unit 34 is configured to include a B-mode image data generation unit 341 which generates the B-mode image data which are an ultrasound image displayed by converting the amplitude of the echo signal to the luminance and a feature image data generation unit 342 which generates the feature image data where the feature calculated by the attenuation correction unit 334b are displayed together with the B-mode image in association with visual information.

The B-mode image data generation unit 341 generates the B-mode image data by performing signal processes using well-known techniques such as a gain process and a contrast process on the B-mode reception data received from the signal processing unit 32 and by performing data culling and the like according to data step width defined according to a display range of the image in the display device 4. The B-mode image is a gray scale image obtained by equalizing values of R (red), G (green), and B (blue) as variables in the case of employing an RGB color system as a color space.

The B-mode image data generation unit 341 generates the B-mode image data by performing coordinate transformation of rearranging so that the scanning range in the B-mode reception data from the signal processing unit 32 can be spatially represented correctly and by filling the empty gap between the B-mode reception data by performing an interpolation between the B-mode reception data. The B-mode image data generation unit 341 outputs the generated B-mode image data to the feature image data generation unit 342.

The feature image data generation unit 342 associates the visual information with the value of the feature calculated by the feature calculation unit 334. Next, the sample data group corresponding to the position of each pixel on the B-mode image data is specified. Next, the visual information associated with the value of the feature calculated from each sample data group is allocated to each pixel. In this manner, the feature image data generation unit 342 allocates the visual information to each pixel in the B-mode image data. A specific allocation method is as follows. First, the feature image data generation unit 342 allocates the visual information corresponding to the feature of the frequency spectrum calculated from the sample data group $F_j$ to the pixel region corresponding to the data amount of one sample data group $F_j$ (j=1, 2, . . . , K), for example, illustrated in FIG. 5. For example, the feature image data generation unit 342 generates the feature image data by associating the hue as visual information with any one of the above-described slope, intercept, and mid-band fit. The feature image data generation unit 342 may generate the feature image data by associating the hue with one of the two feature selected from the slope, intercept, and mid-band fit and by associating the brightness with the other feature. As the visual information associated with the feature, there may be exemplified hue, saturation, brightness, luminance value, variables of a color space constituting a predetermined color system such as R (red), G (green), and B (blue), and the like.

The model information acquisition unit 35 is configured to include an identification unit 351 which identifies the ultrasound endoscope 2 connected to the ultrasound diagnostic apparatus 3 based on the acquired model information of the ultrasound endoscope 2. The identification unit 351 generates a result of identification of the ultrasound endoscope 2 identified based on the information on the model of the ultrasound transducer 21 included in the model information or the information on the machine body of the ultrasound endoscope 2 and outputs the result of identification to the control unit 38.

The correction data selection unit 36 acquires the result of identification of the identification unit 351 through the control unit 38 and selects the correction data of the ultrasound endoscope 2 according to the result of identification by referring to the storage unit 39 (the later-described correction information storage unit 391). The correction data selection unit 36 outputs the information on the selected correction data to the control unit 38.

The control unit 38 is embodied by using a central processing unit (CPU), various types of calculation circuits, or the like having calculation and control functions. The control unit 38 generally controls the ultrasound diagnostic apparatus 3 by reading the information stored in the storage unit 39 from the storage unit 39 and performing various calculation processes associated with operation methods of the ultrasound diagnostic apparatus 3. The control unit 38 may share the common CPU with the signal processing unit 32, the computing unit 33, or the correction data selection unit 36.

The storage unit 39 stores a plurality of features calculated for every frequency spectrum by the attenuation correction unit 334b or the image data generated by the image processing unit 34. The storage unit 39 includes a correction information storage unit 391 which stores the correction data used at the time when the analysis data correction unit 333 corrects the spectral data.

Besides, the storage unit 39 stores, for example, information (a relationship between the amplification factor and the reception depth illustrated in FIG. 2) required for the amplification process, information (a relationship between the amplification factor and the reception depth illustrated in FIG. 4) required for the amplification correction process, information (referred to Formula (1), for example, values of A and $V_c$) required for the logarithmic conversion process, information on a window function (Hamming, Hanning, Blackman, or the like) required for the frequency analysis process, and the like.

The storage unit 39 stores various programs including an operation program for performing operation methods of the ultrasound diagnostic apparatus 3. The operation program may also be recorded in a computer-readable recording medium such as a hard disk drive, a flash memory, a CD-ROM, a DVD-ROM, or a flexible disk to be widely distributed. The above-described various programs may also be acquired by downloading via a communication network.

Herein, the communication network is a network embodied by, for example, existing public network, a local area network (LAN), a wide area network (WAN), or the like, and the communication network may be a wired or wireless network.

The storage unit 39 having the above-described configuration is embodied by using a read only memory (ROM) where various programs and the like are installed in advance, a random access memory (RAM) storing calculation parameters of each process or data, a hard disk drive, or the like.

Figure 8:
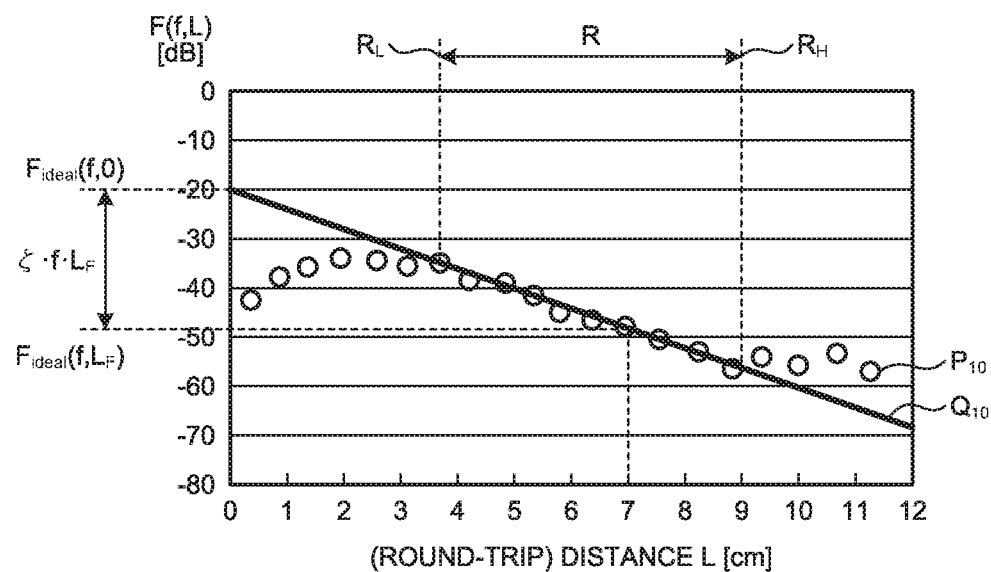
FIG. 8 is a graph illustrating, as a profile of spectral data with respect to a round-trip distance at a certain frequency, an example of observation data obtained through actual observation and theoretical data obtained from the observation data.

Next, the correction of the spectral data performed by the analysis data correction unit 333 will be described. In theory, the echo signal obtained by the ultrasound transducer 21 is exponentially attenuated according to the distance from the ultrasound transducer 21. The signal amplification unit 311 performs the STC correction on the RF data obtained through the A/D conversion of the echo signal so that larger amplification is performed as the reception depth is larger is performed. However, since the influence of the STC correction is cancelled after the RF data passes through the amplification correction unit 331, similarly to the echo signal, the RF data is exponentially attenuated. On the other hand, the spectral data $F(f,L)$ are data obtained by the frequency analysis unit 332 performing logarithmic conversion on the RF data which are exponentially attenuated due to the cancellation of the STC correction. For this reason, the RF data is linearly attenuated according to the distance from the ultrasound transducer 21. In this manner, the exponential attenuation of the echo signal or the RF data before the cancellation of the STC correction is illustrated in Formula (7), and the linear attenuation of the spectral data $F(f,L)$ is illustrated in Formula (9) as described above. However, actually, the near and far regions of the ultrasound transducer 21 do not become linear. FIG. 8 is a graph illustrating, as a profile of the spectral data $F(f,L)$ with respect to the round-trip distance L at a certain frequency, an example of observation values (hereinafter, referred to as observation data) obtained through actual observation and theoretical data obtained from the observation data. In FIG. 8, the horizontal axis is a round-trip distance L (cm) (=2×reception depth z) from the ultrasound transducer 21. In FIG. 8, the vertical axis is a value of the spectral data $F(f,L)$ (decibel expression). In FIG. 8, a plot $P_{10}$ indicated by marks ○ (white circles) is the observation data obtained through the actual observation. Herein, for the convenience of the description, FIG. 8 illustrates an example where focal depth $z_F$ is 3.5 cm and the round-trip distance $L_F$ from the ultrasound transducer 21 to the focus is 7 cm.

Specifically, the frequency analysis unit 332 generates the spectral data $F(f,L)$ given by Formula (1). As described above, actually, since the near and far regions of the ultrasound transducer 21 do not become linear, theoretical data $F_{ideal}(f,L)$ are obtained based on the observation data in a predetermined depth range set according to the round-trip distance. In the embodiment, the predetermined depth range is a variable range which varies with a variable focal position. In the embodiment, in the depth range R with respect to the focal position $(L=L_F)$, the lower limit is denoted by $R_L$, and the upper limit is denoted by $R_H$. By using coefficients $g_1$ and $g_2$, it is set that $R_L=g_1 \times L_F$ $(0.5 \leq g_1 \leq 0.8)$ and $R_H=g_2 \times L_F$ $(1.3 \leq g_2 \leq 2.0)$. Herein, each of $g_1$ and $g_2$ may be arbitrarily set within the range. Since the transmission wave is in phase at the focal depth, the reference can be obtained from a depth where the acoustic characteristics are close to the theoretical values, and thus, it is preferable that the above-described predetermined depth range is set to the focal depth. However, even in the depth range having a small margin including the focal depth, the theoretical data $F_{ideal}(f,L)$ may be calculated.

From Formula (9), the theoretical data $F_{ideal}(f,L)$ is given by the following Formula (14).

$$F_{ideal}(f,L)=F_{ideal}(f,0)-\zeta fL \qquad (14)$$

In this stage, $F_{ideal}(f,0)$, which is the first term of Formula (14), is not obtained. If the theoretical data $F_{ideal}(f,L)$ are obtained as $F_{ideal}(f,0)=F(f,0)$ by using the observation value $F(f,0)$ at $L=0$, it is obvious from FIG. 8 that the calculation is simple, but the error from the observation data is large. That is, the site where the straight line of the theoretical data $F_{ideal}(f,L)$ expressed by Formula (14) is allowed to be fitted to the observation data is not $L=0$, but the site needs to be in a linear attenuation range of the spectral data. Preferably, the site is in a range of $R_L \leq L \leq R_H$, and more preferably, the focal depth L is $L_F$.

In the embodiment, it is assumed that the straight line (straight line $Q_{10}$ illustrated in FIG. 8) fitted to the observation data at the focal position $(L_F)$ is the theoretical data. Specifically, the theoretical data $F_{ideal}(f,L)$ is given based on Formula (14) by the following Formula (15).

$$F_{ideal}(f,L)=F_{ideal}(f,L_F)-\zeta f(L-L_F)=F(f,L_F)-\zeta f(L-L_F) \qquad (15)$$

In the embodiment, the biological observation ultrasound endoscope, the correction ultrasound endoscope, and the standard ultrasound endoscope are defined as follows.

1. Biological observation ultrasound endoscope: a machine body which is actually introduced into a subject in the medical field.

2. Correction ultrasound endoscope: An ultrasound endoscope which is selected for each model of ultrasound endoscopes and is installed in the sites of shipment, quality control, or the like in a factory. Hereinafter, among the correction ultrasound endoscopes, a biological observation ultrasound endoscope and a correction ultrasound endoscope for the same model are particularly called "correction ultrasound endoscopes". The model and sensitivity of the ultrasound transducer included in the correction ultrasound endoscope are the same as those of the ultrasound transducer included in the biological observation ultrasound endoscope. The correction ultrasound endoscope is used as a substitute for the biological observation ultrasound endoscope.

3. Standard ultrasound endoscope: As one machine body which is selected for one model, a machine body for reference which allows the sensitivity of the ultrasound transducer of the correction ultrasound endoscope or the biological observation ultrasound endoscope to be coincident with the sensitivity of the ultrasound transducer of the standard ultrasound endoscope at every frequency.

In the embodiment, the correction data calculation unit 335 generates the theoretical data $F_{ideal}(f,L)$ based on the observation data obtained by the standard ultrasound endoscope and the correction ultrasound endoscope imaging the reference phantom, obtains a difference $\Delta F$ in sensitivity of each ultrasound endoscope, and uses the difference in sensitivity as the correction data. In the description hereinafter, the correction data is calculated by using the biological observation ultrasound endoscope, but the biological observation ultrasound endoscope may be used as the correction ultrasound endoscope.

The reference phantom is formed, for example, by uniformly mixing and distributing a material with adjusting the size, the number density, and the scattering intensity of scatterers and solidifying the material, and it is known in advance that the attenuation rate $\zeta_s$ [dB/cm/MHz] is also uniform.

In the description hereinafter, as spectral data obtained, for example, at the time when the standard ultrasound endoscope ($S_S$) images the reference phantom ($Phn_S$), the spectral data in a case where the parameters are the frequency f and the round-trip distance L are denoted by $F(S_S, Phn_S; f, L)$. Similarly, in the case of the correction ultrasound endoscope ($S_C$), the spectral data is denoted by $F(S_C, Phn_S; f, L)$, and in the case of the biological observation ultrasound endoscope ($S_{LB}$), the spectral data is denoted by $F(S_{LB}, Phn_S; f, L)$.

Figure 9:
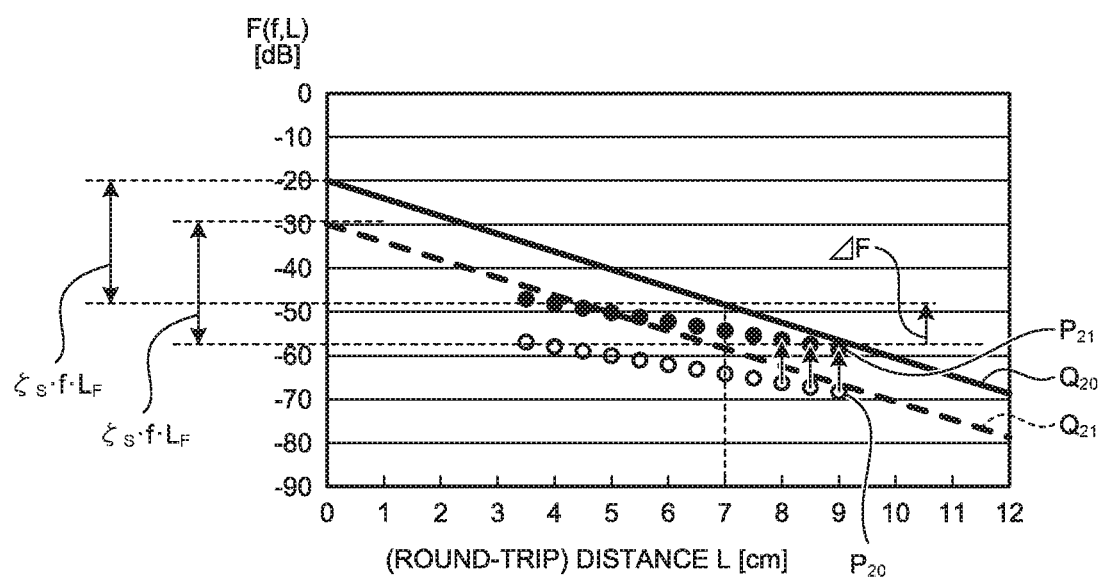
FIG. 9 is a graph illustrating, as a profile with respect to a round-trip distance at a certain frequency, an example of observation data obtained through actual observation and corrected observation data.

FIG. 9 is a graph illustrating, as a profile with respect to the round-trip distance L at a certain frequency, an example of the observation data obtained through actual observation and corrected observation data. In FIG. 9, the horizontal axis is a round-trip distance L (cm). In FIG. 9, the vertical axis is spectral data F(f,L) (decibel expression). In FIG. 9, a straight line $Q_{20}$ indicates the theoretical data $F_{ideal}(S_S, Phn_S; f, L)$ obtained at the time when the standard ultrasound endoscope ($S_S$) images the reference phantom ($Phn_S$), and a broken line $Q_{21}$ indicates the theoretical data $F_{ideal}(S_C, Phn_S; f, L)$ obtained at the time when the correction ultrasound endoscope ($S_C$) images the reference phantom ($Phn_S$). In FIG. 9, a plot $P_{20}$ indicated by marks ○ is the observation data obtained by the biological observation ultrasound endoscope ($S_{LB}$). The observation data $P_{20}$ are obtained from a living body by using the biological observation ultrasound endoscope ($S_{LB}$). The attenuation rate of the living body is different from the attenuation rate $\zeta_S$ of reference phantom. The echo signal intensity from the living body is also different from the echo signal intensity from the phantom. For this reason, in FIG. 9, the position or slope of the plot group of the observation data $P_{20}$ indicated by marks ○ is different from the position or slope of the straight line $Q_{20}$ indicated by the theoretical data $F_{ideal}(S_S, Phn_S; f, L)$ of the standard ultrasound endoscope ($S_S$) and is different from the position or slope of the straight line $Q_{21}$ indicated by the theoretical data $F_{ideal}(S_C, Phn_S; f, L)$ of the correction ultrasound endoscope ($S_C$).

By using the Formula (15), the theoretical data $F_{ideal}(S_S, Phn_S; f, L)$ of the standard ultrasound endoscope ($S_S$) are given by the following Formula (16).

$$F_{ideal}(S_S, Phn_S; f, L) = F(S_S, Phn_S; f, L_F) - \zeta_S \cdot f \cdot (L - L_F) \quad (16)$$

Herein, $\zeta_S$ is an attenuation rate per unit distance and per unit frequency according to the reference phantom ($Phn_S$), and the unit thereof is, for example, [dB/cm/MHz].

On the other hand, by using the above-described Formula (15), the theoretical data $F_{ideal}(S_C, Phn_S; f, L)$ of the correction ultrasound endoscope ($S_C$) is given by the following Formula (17).

$$F_{ideal}(S_C, Phn_S; f, L) = F(S_C, Phn_S; f, L_F) - \zeta_S \cdot f \cdot (L - L_F) \quad (17)$$

The theoretical data $F_{ideal}(S_S, Phn_S; f, L)$ and $F_{ideal}(S_C, Phn_S; f, L)$ expressed by Formulas (16) and (17) become straight lines obtained by observing the reference phantom ($Phn_S$) and fitting to the respective observation data $F(S_S, Phn_S; f, L_F)$ and $F(S_C, Phn_S; f, L_F)$ obtained at the common focal position ($L_F$).

Since the transmission wave is in phase at the common focal depth, and thus, the reference can be obtained from the depth where the acoustic characteristics are close to the theoretical values, and thus, the common focal depth is preferred. However, a straight line where the theoretical data $F_{ideal}(S_S, Phn_S; f, L)$ and $F_{ideal}(S_C, Phn_S; f, L)$ are fitted to the observation data at the position different from the focal depth ($L_F$) may be used.

The theoretical data $F_{ideal}(S_S, Phn_S; f, L)$ and $F_{ideal}(S_C, Phn_S; f, L)$ are set to be at the common focal depth, so that the same correction data can be used for observation data at different focal positions. Accordingly, it is possible to reduce the correction data amount stored in the correction information storage unit 391.

As is clear from Formulas (2) and (16), two straight lines $Q_{20}$ and $Q_{21}$ indicating the theoretical data $F_{ideal}(S_S, Phn_S; f, L)$ and $F_{ideal}(S_C, Phn_S; f, L)$ have the same slope of $-\zeta_S \cdot f$ with respect to the round-trip distance L and are parallel to each other (refer to FIG. 9). It can be understood from the above description that the standard ultrasound endoscope ($S_S$) and the correction ultrasound endoscope ($S_C$) can correct the difference in sensitivity by the correction data depending on the frequency of the ultrasound wave without depending on the reception depth (round-trip distance L).

A difference $\Delta F$ in sensitivity between the standard ultrasound endoscope ($S_S$) and the correction ultrasound endoscope ($S_C$) is given as a difference between Formula (16) and Formula (17) by the following Formula (18).

$$\Delta F = F_{ideal}(S_S, Phn_S; f, L) - F_{ideal}(S_C, Phn_S; f, L) = F(S_S, Phn_S; f, L_F) - F(S_C, Phn_S; f, L_F) \quad (18)$$

As illustrated in Formula (18), the difference $\Delta F$ in sensitivity between the standard ultrasound endoscope ($S_S$) and the correction ultrasound endoscope ($S_C$) is independent of the round-trip distance L. In the embodiment, first, before the ultrasound diagnostic apparatus 3 is used for the subject such as a living body, in the sites of shipment, quality control, or the like, the reference phantom ($Phn_S$) is imaged by the standard ultrasound endoscope ($S_S$) and the correction ultrasound endoscope ($S_C$) in advance. The correction data calculation unit 335 calculates the theoretical data $F_{ideal}(S_S, Phn_S; f, L_F)$ and the $F_{ideal}(S_C, Phn_S; f, L_F)$ from the data at the focal depths of the two ultrasound endoscopes, calculates the difference $\Delta F$ in sensitivity by subtracting two theoretical data, and outputs the difference in sensitivity to the correction information storage unit 391 through the control unit. The correction information storage unit 391 stores the difference $\Delta F$ in sensitivity as the correction data. The correction information storage unit 391 stores the correction data for every model of the correction ultrasound endoscope of which model is the same as the model (model which can be identified by the identification unit 351) which can be used as the biological observation ultrasound endoscope actually introduced into the subject.

Next, when the ultrasound diagnostic apparatus 3 is used for the subject such as a living body, the analysis data correction unit 333 acquires the correction data (difference $\Delta F$ in sensitivity) selected by the correction data selection unit 36 by referring to the correction information storage unit 391 and performs the correction of the observation data by adding the difference $\Delta F$ in sensitivity to the observation data (plot $P_{20}$) obtained by the biological observation ultrasound endoscope ($S_{LB}$). In FIG. 9, the corrected observation data is a plot $P_{21}$ indicated by marks ● (black circles) and are increased by $\Delta F$ from the uncorrected plot $P_{20}$ indicated by marks ○.

Figure 10:
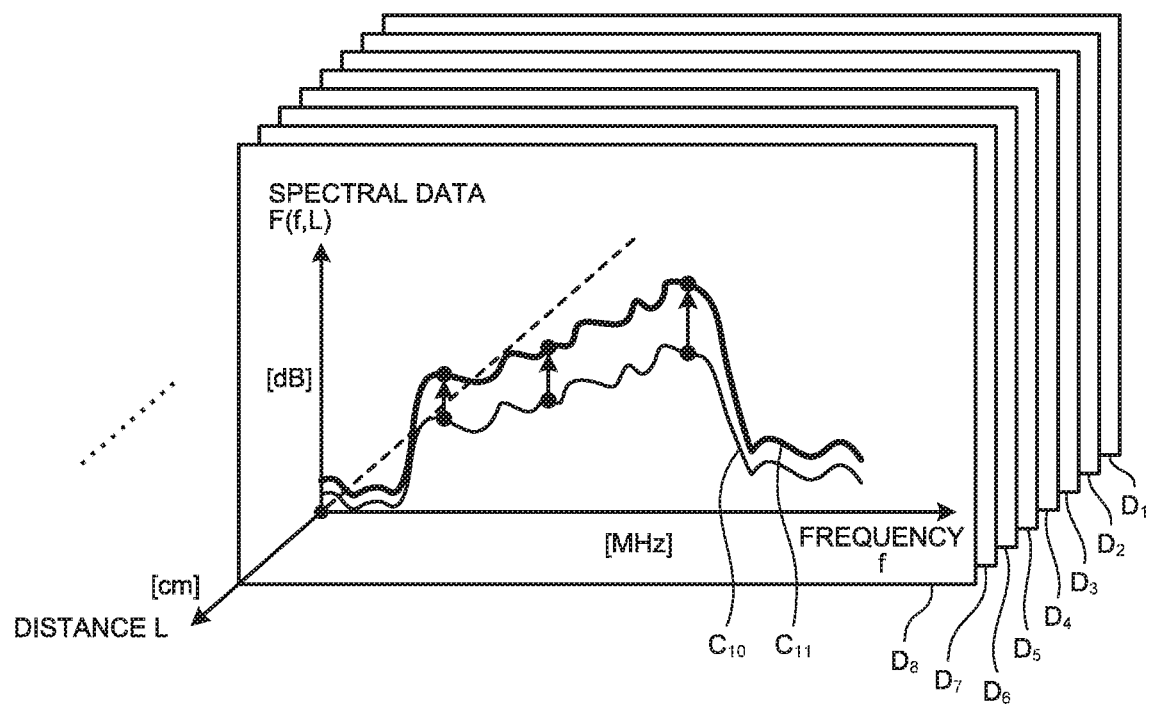
FIG. 10 is a schematic diagram illustrating correction of analysis data performed by an analysis data correction unit.

FIG. 10 is a schematic diagram illustrating the correction of the analysis data performed by the analysis data correction unit 333. The analysis data correction unit 333 corrects a plurality of frequency spectra calculated by the frequency analysis unit 332 by using the correction data (difference $\Delta F$ in sensitivity) determined for every frequency.

Specifically, the analysis data correction unit 333 corrects the observation data $F(S_{LB}, Phn_S; f, L)$ by adding the correction data (difference $\Delta F(f)$ in sensitivity) determined for every frequency to the respective data $D_1, D_2, D_3, D_4, D_5, D_6, D_7, D_8, \ldots$ of the reception depths (round-trip distances L) of a plurality of spectral data calculated by the frequency analysis unit 332. The corrected observation data $F'(S_{LB}, Phn_S; f, L)$ are given by the following Formula (19).

$$F'(S_{LB}, Phn_S; f, L) = F(S_{LB}, Phn_S; f, L) + \Delta F(f) = F(S_{LB}, Phn_S; f, L) + F(S_S, Phn_S; f, L_F) - F(S_C, Phn_S; f, L_F) \quad (19)$$

Herein, the above-described Formula (18) is used.

As illustrated in FIG. 10, for example, with respect to the data $D_8$ which are spectral data in a certain round-trip distance (reception depth), the corrected spectral data $C_{11}$ is generated by adding the correction data (difference $\Delta F(f)$ in sensitivity) defined for each frequency to the uncorrected spectral data $C_{10}$.

After that, the feature calculation unit 334 calculates the feature using the corrected spectral data output from the analysis data correction unit 333. Accordingly, it is possible to calculate the feature without depending on the difference in sensitivity of the ultrasound endoscope 2. That is, although any model of the biological observation ultrasound endoscope is used for a subject, it is possible to obtain the feature having the same values as those in the case of using the standard ultrasound endoscope.

Figure 11:
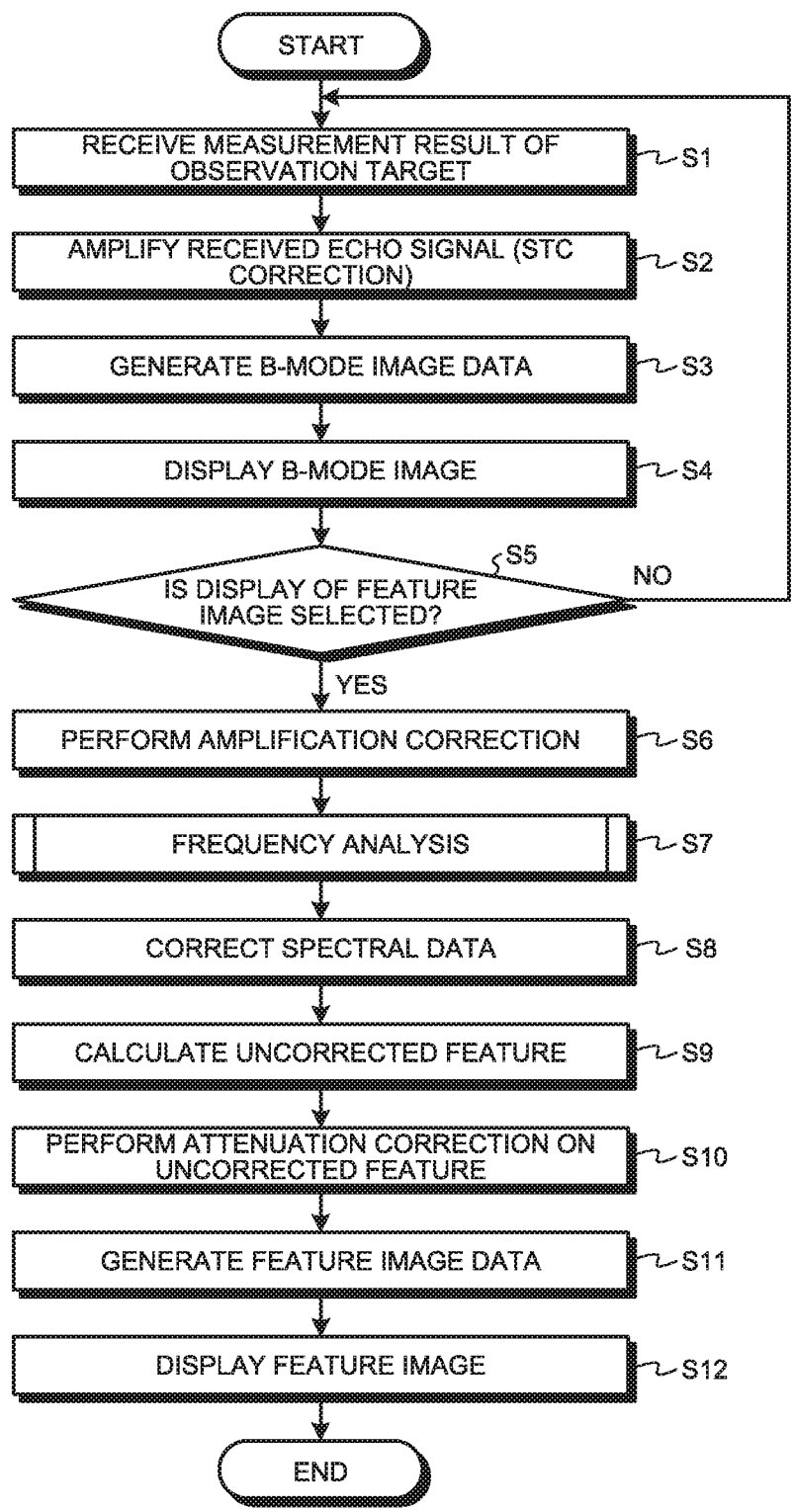
FIG. 11 is a flowchart illustrating an overview of processes performed by the ultrasound diagnostic apparatus according to the embodiment of the present invention.

FIG. 11 is a flowchart of an overview of processes performed by the ultrasound diagnostic apparatus 3 having the above-described configuration. First, the ultrasound diagnostic apparatus 3 receives an echo signal as a measurement result of an observation target by the ultrasound transducer 21 from the ultrasound endoscope 2 (step S1).

The signal amplification unit 311 which receives the echo signal from the ultrasound transducer 21 performs amplification of the echo signal (step S2). Herein, the signal amplification unit 311 performs amplification (STC correction) of the echo signal based on the relationship between the amplification factor and the reception depth illustrated in FIG. 2. Next, the transmitting and receiving unit 31 generates RF data by sampling and discretizing the echo signal at an appropriate sampling frequency (for example, 50 MHz) and outputs the RF data to the B-mode image data generation unit 341 and the amplification correction unit 331.

Subsequently, the B-mode image data generation unit 341 generates the B-mode image data by using the RF data output from the transmitting and receiving unit 31 and outputs the B-mode image data to the feature image data generation unit 342. The feature image data generation unit 342 does not apply any process on the B-mode image data and outputs the B-mode image data to the display device 4 as it is (step S3). The display device 4 which receives the B-mode image data displays the B-mode image corresponding to the B-mode image data (step S4).

After that, the control unit 38 checks which one of "display" and "non-display" of the feature image is selected by a user such as an operator through a button or menu (not illustrated) of the input unit 37 (step S5). If it is checked that "display" is selected, the control unit 38 outputs a feature image production start command to each components constituting the computing unit 33 (Yes in step S5). If it is checked that "non-display" is selected, the feature image production start command is not issued (No in step S5). When receiving the feature image production start command, each component of the computing unit 33 performs the process of step S6 and the following processes described later. Irrespective of the presence or absence of the feature image production start command, the transmitting and receiving unit 31, the signal amplification unit 311, the signal processing unit 32, the B-mode image data generation unit 341, and the feature image data generation unit 342 of the ultrasound diagnostic apparatus 3 repeat the processes of steps S1 to S4 described above. For this reason, while the user instructs "non-display" of the feature image to the input unit 37, the B-mode image is displayed in the display device 4 repetitively for every scan in the subject performed by the ultrasound transducer 21.

In a case where each component of the computing unit 33 receives the feature image production start command, first, the amplification correction unit 331 performs the amplification correction of the RF data output from the transmitting and receiving unit 31 with a constant amplification factor irrespective of the reception depth (step S6). Herein, the amplification correction unit 331 performs the amplification correction so that the relationship between the amplification factor and the reception depth illustrated in, for example, FIG. 4 is satisfied.

Figure 12:
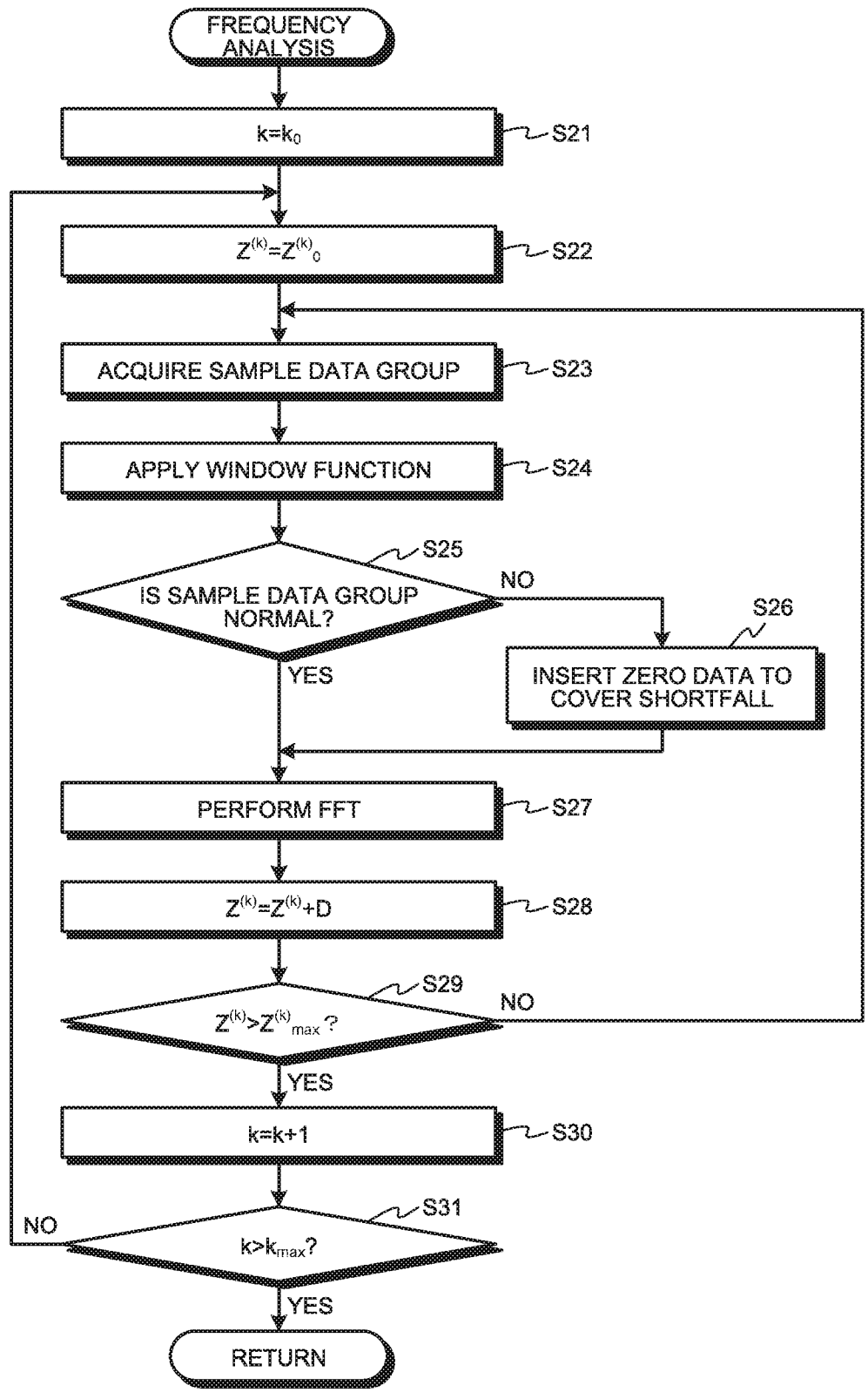
FIG. 12 is a flowchart illustrating an overview of processes performed by a frequency analysis unit of the ultrasound diagnostic apparatus according to the embodiment of the present invention.

After that, the frequency analysis unit 332 calculates the spectral data for all the sample data groups by performing the frequency analysis through the FFT (step S7: analysis step). FIG. 12 is a flowchart illustrating an overview of the processes performed by the frequency analysis unit 332 in step S7. Hereinafter, the frequency analysis process will be described in detail with reference to the flowchart illustrated in FIG. 12.

First, the frequency analysis unit 332 sets a counter k identifying the sound ray as an analysis object to $k_0$ (step S21). The initial value $k_0$ is the number of the sound ray at the rightmost side of the analysis range in FIG. 3.

Subsequently, the frequency analysis unit 332 sets the initial value $Z^{(k)}_0$ of the data position (corresponding to the reception depth) $Z^{(k)}$ representing a series of data groups (sample data groups) acquired for the FFT (step S22). For example, as described above, FIG. 5 illustrates the case where the eighth data position of the sound ray $SR_k$ is set as the initial value $Z^{(k)}_0$. The initial value $Z^{(k)}_0$ is the shallowest reception depth in the analysis range on the sound ray $SR_k$.

After that, the frequency analysis unit 332 acquires the sample data group (step S23) and applies the window function stored in the storage unit 39 to the acquired sample data group (step S24). In this manner, by applying the window function to the sample data group, the sample data group is prevented from being discontinuous at the boundary, so that the occurrence of artifact can be prevented.

Subsequently, the frequency analysis unit 332 determines whether or not the sample data group of the data position $Z^{(k)}$ is a normal data group (step S25). As described with reference to FIG. 5, the sample data group needs to have the number of data that is two to the powers. Hereinafter, it is assumed that the number of data in the normal sample data group is $2^n$ (n is a positive integer). in the embodiment, the data position $Z^{(k)}$ is set to be near to the center of the sample data group including the $Z^{(k)}$ as near as possible. Specifically, since the number of data in the sample data group is $2^n$, the $Z^{(k)}$ is set to be $2^n/2$ ($=2^{n-1}$)-th position near to the center of the sample data group. In this case, the configuration where the sample data group is normal denotes that there are $2^{n-1}-1$ ($=N$) data in the side shallower than the data position $Z^{(k)}$ and there are $2^{n-1}$ ($=M$) data in the side deeper than the data position $Z^{(k)}$. In the case illustrated in FIG. 5, all the sample data groups $F_1, F_2, F_3, \ldots,$ and $F_{K-1}$ are normal. FIG. 5 illustrates the case of n=4 (N=7, M=8).

As a result of the determination in step S25, in a case where the sample data group of the data position $Z^{(k)}$ is normal (Yes in step S25), the frequency analysis unit 332 proceeds to step S27 described later.

As a result of the determination in step S25, in a case where the sample data group of the data position $Z^{(k)}$ is not normal (No in step S25), the frequency analysis unit 332 generates a normal sample data group by inserting zero data to cover shortfall (step S26). Before the zero data is added, a window function is applied to the sample data group (for example, the sample data group $F_K$ in FIG. 5) which is determined not to be normal in step S25. For this reason, although the zero data is inserted into the sample data group, discontinuity of the data does not occur. After step S26, the frequency analysis unit 332 proceeds to step S27 described later.

In step S27, the frequency analysis unit 332 obtains the spectral data which are a frequency distribution of the amplitude by performing the FFT by using the sample data group (step S27).

Subsequently, the frequency analysis unit 332 changes the data position $Z^{(k)}$ by using the step width D (step S28). With respect to the step width D, it is assumed that an operator's input value through the input unit 37 is stored in the storage unit 39 in advance. FIG. 5 illustrates the case of D=15. It is preferable that the step width D is as small as possible and, particularly, is equal to the data step width used at the time when the B-mode image data generation unit 341 generates the B-mode image data. However, in a case where the calculation amount in the frequency analysis unit 332 desires to be reduced, a value larger than the data step width may be set as the step width D.

Next, the frequency analysis unit 332 determines whether or not the data position $Z^{(k)}$ is larger than the maximum value $Z^{(k)}_{max}$ on the sound ray $SR_k$ (step S29). The maximum value $Z^{(k)}_{max}$ is the deepest reception depth in the analysis range on the sound ray $SR_k$. In a case where the data position $Z^{(k)}$ is larger than the maximum value $Z^{(k)}_{max}$ (Yes in step S29), the frequency analysis unit 332 increases the counter k by 1 (step S30). This denotes that the process is moved to the adjacent sound ray. On the other hand, the data position $Z^{(k)}$ is equal to or smaller than the maximum value $Z^{(k)}_{max}$ (No in step S29), the frequency analysis unit 332 returns to step S23.

After step S30, the frequency analysis unit 332 determines whether or not the counter k is larger than the maximum value $k_{max}$ (step S31). In a case where the counter k is larger than the $k_{max}$ (Yes in step S31), the frequency analysis unit 332 ends a series of the frequency analysis processes. On the other hand, in a case where the counter k is equal to or smaller than $k_{max}$ (No in step S31), the frequency analysis unit 332 returns to step S22. The maximum value $k_{max}$ is the number of the sound ray in the leftmost side of the analysis range in FIG. 3.

In this manner, the frequency analysis unit 332 performs the FFT on each of the ($k_{max}-k_0+1$) sound rays in the analysis object range several times for each depth. A result of the FFT together with the reception depth and the reception direction is stored in the correction information storage unit 391

Furthermore, with respect to the four types of values $k_0$, $k_{max}$, $Z^{(k)}_0$, and $Z^{(k)}_{max}$ the default values including the entire scan range of FIG. 3 are stored in the storage unit 39 in advance, and thus, the frequency analysis unit 332 appropriately reads the values and performs the process of FIG. 12. In a case where the default values are read, the frequency analysis unit 332 performs the frequency analysis process on the entire scan range. However, the four types of values $k_0$, $k_{max}$, $Z^{(k)}_0$, and $Z^{(k)}_{max}$ can be changed by user's (operator's) input of instruction to the region of interest through the input unit 37. In a case where the values are changed, the frequency analysis unit 332 performs the frequency analysis process on only the region of interest to which the instruction is input.

Subsequently to the above-described frequency analysis process of step S7, the analysis data correction unit 333 reads the correction data stored in the correction information storage unit 391 in advance. Next, a plurality of spectral data calculated by the frequency analysis unit 332 is corrected based on the correction data (step S8: correction step). The spectral data $C_1$ illustrated in FIG. 6 are example of the spectral data obtained as a result of step S8. At this time, the analysis data correction unit 333 acquires the correction data selected by the correction data selection unit 36 and performs correction of the analysis data according to the difference $\Delta F$ in the sensitivity which is set for each model.

After that, the feature calculation unit 334 calculates each of the uncorrected feature for a plurality of spectral data corrected by the analysis data correction unit 333 and calculates the feature of each of the spectral data by performing the attenuation correction of removing the influence of the attenuation of the ultrasound wave from the uncorrected feature of each of the spectral data (steps S9 and S10).

In step S9, the approximation unit 334a calculates the uncorrected feature corresponding to each of the spectral data by performing the regression analysis on a plurality of spectral data generated by the analysis data correction unit 333 (step S9). Specifically, the approximation unit 334a calculates the slope $a_0$, intercept $b_0$, and mid-band fit $c_0$ as the uncorrected feature by approximating each of the spectral data by using the linear equation by the regression analysis. For example, the straight line $L_{10}$ illustrated in FIG. 7 is a regression straight line obtained by the approximation unit 334a approximating the spectral data $C_1$ in the frequency band U by the regression analysis.

Subsequently, the attenuation correction unit 334b calculates an attenuation-corrected feature by performing the attenuation correction, using the attenuation rate $\zeta$, on the uncorrected feature obtained by the approximation unit 334a approximating each of the spectral data and stores the attenuation-corrected feature in the storage unit 39 (step S10). The straight line $L_1$ illustrated in FIG. 7 is an example of the straight line obtained by the attenuation correction unit 334b performing the attenuation correction process.

In step S10, the attenuation correction unit 334b calculates the attenuation-corrected feature by substituting the data position $Z=(v_s/(2 \cdot f_{sp})) \cdot D \cdot n + Z_0$ obtained by using the data arrangement of the sound ray of the ultrasound signal into the reception depth z in the Formulas (10) and (12). Herein, $f_{sp}$ is a sampling frequency of the data, $v_s$ is a velocity of sound, D is a data step width, n is the number of steps from the first data of the sound ray to the data position of the sample data group as the process object, and $Z_0$ is the shallowest reception depth in the analysis range. For example, when the sampling frequency $f_{sp}$ of the data is set to 50 MHz, the velocity of sound $v_s$ is set to 1530 m/sec, and the step width D is set to 15 by employing the data arrangement illustrated in FIG. 5, $z=0.2295$ n+$Z_0$ (mm).

The feature image data generation unit 342 generates the feature image data by superposing the visual information (for example, hue) associated with the feature calculated in step S9 on each pixel of the B-mode image data generated by the B-mode image data generation unit 341 (step S11).

Figure 13:
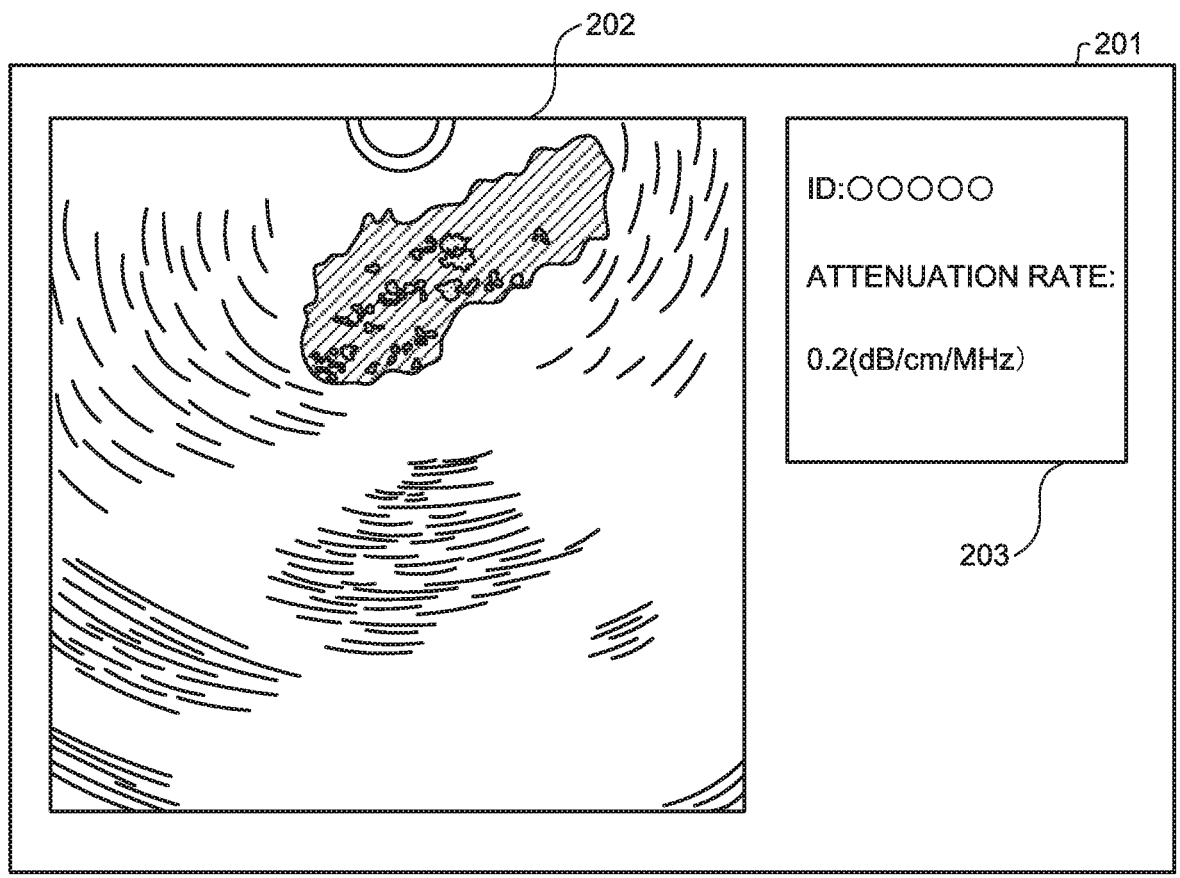
FIG. 13 is a schematic diagram illustrating a display example of a feature image in a display device of the ultrasound diagnostic apparatus according to the embodiment of the present invention.

After that, the display device 4 displays the feature image corresponding to the feature image data generated by the feature image data generation unit 342 under the control of the control unit 38 (step S12). FIG. 13 is a schematic diagram illustrating a display example of the feature image in the display device 4. A feature image 201 illustrated in FIG. 13 has a superposed image display portion 202 displaying an image where the visual information on the feature is superposed on the B-mode image and an information display portion 203 displaying identification information of the observation target or the like. Information on the feature, information on the approximation equation, image information such as gain and contrast, or the like may be further displayed on the information display portion 203. The B-mode image corresponding to the feature image may be displayed to be aligned with the feature image.

In a series of the processes described heretofore (steps S1 to S12), the process of step S2 and the processes of steps S4 to S10 may be performed in parallel.

According to the embodiment of the present invention described above, by using any one of the biological observation ultrasound endoscope actually introduced into a subject and the correction ultrasound endoscope of which the model and the sensitivity of the ultrasound transducer are the same as those of the biological observation ultrasound endoscope, the frequency analysis unit 332 calculates the observation data of the spectral data based on the echo signal received from the reference reflector, and the correction data calculation unit 335 calculates the theoretical data based on the observation data. By using the standard ultrasound endoscope as a reference of sensitivity adjustment, similarly, the frequency analysis unit 332 calculates the observation data based on the echo signal received from the reference reflector, and the correction data calculation unit 335 calculates the theoretical data based on the observation data. The correction data calculation unit 335 calculates the difference between the two theoretical data and stores the difference as the correction data in the correction information storage unit 391 in advance. After that, when the biological observation ultrasound endoscope is introduced into the subject, the frequency analysis unit 332 calculates the observation data of the subject based on the echo signal received from the subject, the analysis data correction unit 333 corrects the spectral data by reading the correction data from the correction information storage unit 391 and adding the correction data to the observation data of the biological observation ultrasound endoscope. For this reason, it is possible to acquire the analysis values which do not depend on the difference in characteristics between the ultrasound transducers and of which objectivity is guaranteed. Therefore, without attenuation of the frequency feature or the feature image (color or the like) and without depending on the difference in characteristics such as a difference in sensitivity of the ultrasound transducer, it is possible to reflect information on the tissue objectively and reliably as much as possible.

The frequency analysis unit 332 changes $k_0$ and $k_{max}$ defining the sound ray width and $Z^{(k)}_0$ and $Z^{(k)}_{max}$ defining the depth width according to the user's (operator's) instruction input for the region of interest through the input unit 37, and thus, the spectral data for only the region of interest partitioned by specific depth width and sound ray width with the instruction being input can be calculated and corrected. Therefore, the calculation amount associated with the correction can be decreased, and the frame rate can be increased. Herein, the region of interest is partitioned to be in a fan shape by the depth width and the sound ray width. But not limited to the example, the region of interest may be in a shape of a rectangle or an ellipse, and other shapes may be employed. In this case, the feature calculation unit 334 may be allowed to individually set optimal amplification factors inside the set region of interest and outside the region of interest.

Modified Example of Embodiments

Subsequently, a modified example of the embodiment of the present invention will be described. In the above-described embodiment, the spectral data is corrected by the analysis data correction unit 333, and after that, the feature calculation unit 334 calculates the feature of each of the spectral data. However, in the modified example, the feature calculation unit 334 calculates the feature of each of the spectral data, and after that, the analysis data correction unit 333 corrects the difference of the calculated feature caused by the difference in sensitivity of the ultrasound transducer.

In the modified example, the feature calculation unit 334 calculates the feature a, b, and c based on a plurality of spectral data (analysis data) calculated by the frequency analysis unit 332 by Formulas (10) to (12), and the analysis data correction unit 333 performs correction on each of the calculated feature a, b, and c.

Since it is known that the feature a obtained by Formula (10) are a partial derivative of the spectral data F(f,L) at the frequency f, the following Formula (20) for the corrected feature (slope) a' is derived from Formula (19).

$$a'(S_{LB}, Phn_S; f, L) = a(S_{LB}, Phn_S; f, L) + a(S_S, Phn_S; f, L_F) - a(S_C, Phn_S; f, L_F) \tag{20}$$

Since it is known that the feature c obtained by Formula (12) is an integral value of the spectral data F(f,L) over the range (frequency band) $U(f_L \sim f_H)$ (refer to FIG. 7) at the frequency f, the following Formula (21) for the corrected feature (mid-band fit) c' is derived from Formula (19).

$$c'(S_{LB}, Phn_S; f, L) = c(S_{LB}, Phn_S; f, L) + c(S_S, Phn_S; f, L_F) - c(S_C, Phn_S; f, L_F) \tag{21}$$

Since the feature b obtained by Formula (11) is a linear combination (refer to Formula (12)) of the feature a and c, the following Formula (22) for the corrected feature (intercept) b' is derived from Formulas (20) and (21).

$$b'(S_{LB}, Phn_S; f, L) = b(S_{LB}, Phn_S; f, L) + b(S_S, Phn_S; f, L_F) - b(S_C, Phn_S; f, L_F) \tag{22}$$

According to the modified example, with respect to the features a, b, and c calculated by the feature calculation unit 334, the analysis data correction unit 333 calculates the corrected features a', b', and c' by Formulas (20) to (22), and thus, similarly to the above-described embodiment, it is not necessary to obtain all the observation data $F(S_{LB}, Phn_S; f, L)$ and the like. Therefore, the FFT calculation amount is reduced, so that it is possible to perform the calculation process at a higher speed.

Although the modes for carrying out the present invention have been described, the present invention is not limited to the above-described embodiments. For example, the ultrasound diagnostic apparatus may be configured by connecting circuits having functions via a bus or may be configured by embedding some functions in a circuit structure having other functions.

In the embodiment, the ultrasound endoscope including an optical system such as a light guide is used as an ultrasound probe. The ultrasound probe is not limited to the ultrasound endoscope 2, but the ultrasound probe may be an ultrasound probe including no imaging optical system and no imaging device. Furthermore, as the ultrasound probe, a small-diameter ultrasound miniature probe including no optical system may be employed. In general, the ultrasound miniature probe is inserted into biliary tract, bile duct, pancreatic duct, trachea, bronchus, urethra, or ureter to be used for observing peripheral organs (pancreas, lung, prostate, bladder, lymph node, or the like).

An extracorporeal ultrasound probe which illuminates the subject from the body surface of the subject with the ultrasound wave may be employed as the ultrasound probe. In general, the extracorporeal ultrasound probe is used to be in direct contact with the body surface at the time of observing abdominal organs (liver, gall bladder, bladder, and the like), breast (in particular, mammary gland), and thyroid.

The ultrasound transducer may be a linear vibrator, a radial vibrator, or a convex vibrator. In a case where the ultrasound transducer is a linear vibrator, the scan region is in a shape of a rectangle (rectangle or square). In a case where the ultrasound transducer is a radial vibrator or a convex vibrator, the scan region is in a shape of a fan or a ring. The ultrasound endoscope may allow the ultrasound transducer to mechanically scan. Alternatively, as the ultrasound transducers, a plurality of elements may be arranged in an array shape, and the elements associated with transmission and reception may be electronically exchanged, or delay is provided to the transmission and reception of each element, so that the ultrasound transducer may be allowed to electronically scan.

In the above-described embodiment, the correction data calculation unit 335 is provided inside the ultrasound diagnostic apparatus 3, and the correction data calculation unit 335 generates the correction data based on the theoretical data $F_{ideal}(f,L)$. However, another configuration (for example, the frequency analysis unit 332 or the analysis data correction unit 333) of the calculation unit or an external calculation device may generate the correction data, and the correction information storage unit 391 may store the correction data in advance. In the description, the correction information storage unit 391 stores the correction data for every model. However, at least one of the following combinations may be stored.

1. The theoretical data (first reference data) of the biological observation ultrasound endoscope and the theoretical data (second reference data) of the standard ultrasound endoscope
2. The theoretical data (first reference data) of the correction ultrasound endoscope and the theoretical data (second reference data) of the standard ultrasound endoscope
3. The theoretical data (first reference data) of the correction ultrasound endoscope and the correction data,
4. The theoretical data (first reference data) of the biological observation ultrasound endoscope and the correction data For example, in a case where the first reference data and the second reference data are stored (the correction data is not stored), the correction data calculation unit 335 may read the first reference data of the same model as that of the biological observation ultrasound endoscope identified by the identification unit 351 from the correction information storage unit 391 and may generate the correction data by using the read first reference data and the second reference data every time.

In the above-described embodiment, the feature image data is generated by superposing the visual information associated with the feature calculated by the feature calculation unit 334 on each pixel of the image of the B-mode image data, and the display device 4 displays the feature image data. However, the feature image data and the B-mode image data may be displayed side by side.

According to some embodiments, it is possible to acquire analysis values which do not depend on a difference in characteristics between ultrasound transducers to ensure objectivity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnostic apparatus for generating an ultrasound image based on an ultrasound signal acquired by an ultrasound probe having an ultrasound transducer, the ultrasound transducer being configured to transmit an ultrasound wave to an observation target and to receive the ultrasound wave reflected from the observation target, the ultrasound diagnostic apparatus comprising:
    a processor comprising hardware, the processor being configured to:
        generate analysis data based on the ultrasound signal received from the observation target; and
        correct the analysis data by using correction data based on first reference data and second reference data,
        the first reference data being obtained from an ultrasound signal received from a reference reflector by using the ultrasound transducer or another ultrasound transducer of a same model as that of the ultrasound transducer,
        the second reference data being obtained from the ultrasound signal received from the reference reflector by using a specific ultrasound transducer provided in a standard ultrasound endoscope that is selected for one model and allows sensitivity of the another ultrasound transducer or the ultrasound transducer to be coincident with sensitivity of the specific ultrasound transducer at every frequency.

2. The ultrasound diagnostic apparatus according to claim 1,
    wherein the processor is configured to calculate the correction data based on the first reference data and the second reference data obtained from at least one predetermined common depth of the reference reflector.

3. The ultrasound diagnostic apparatus according to claim 2,
    wherein the processor is configured to calculate the correction data based on the first reference data and the second reference data obtained from a focal depth by using the at least one predetermined common depth.

4. The ultrasound diagnostic apparatus according to claim 1,
    wherein, based on data depending on a frequency of the ultrasound wave as the correction data, the processor is configured to correct the analysis data for each reception depth and each frequency.

5. The ultrasound diagnostic apparatus according to claim 1,
    wherein the processor is configured to correct the analysis data by using frequency spectral data as the first reference data, the second reference data, and the correction data.

6. The ultrasound diagnostic apparatus according to claim 2,
    wherein the processor is configured to set the at least one predetermined common depth such that the at least one predetermined common depth falls within a predetermined depth range including a focal depth of at least one spectral data of the first reference data, the second reference data, and the correction data.

7. The ultrasound diagnostic apparatus according to claim 1,
wherein the processor is configured to generate, as the analysis data, frequency spectral data or frequency feature for displaying tissue characteristics of the observation target.

8. The ultrasound diagnostic apparatus according to claim 1, further comprising a storage configured to store at least one of the first reference data, the second reference data, and the correction data.

9. The ultrasound diagnostic apparatus according to claim 8,
wherein the storage is configured to store, as the correction data, a difference between the first reference data and the second reference data, and
wherein the processor is configured to add the difference to the analysis data newly calculated based on an echo signal obtained from the observation target, thereby to correct the analysis data.

10. The ultrasound diagnostic apparatus according to claim 8,
wherein the storage is configured to store the first reference data and the second reference data, and
wherein the processor is configured to calculate, as the correction data, a difference between the first reference data and the second reference data.

11. The ultrasound diagnostic apparatus according to claim 2,
wherein the processor is configured to perform correction by using the correction data irrespective of a reception depth by using, as the correction data, a difference between the first reference data and the second reference data calculated based on echo signals obtained from at least one specific common depth of the reference reflector.

12. The ultrasound diagnostic apparatus according to claim 8,
wherein the storage is configured to store, in advance, multiple types of correction data associated with multiple types of ultrasound transducers, respectively, and
wherein the processor is configured to:
acquire information on one or more ultrasound transducers connected to the ultrasound diagnostic apparatus; and select one or more of the multiple types of correction data stored in the storage, associated with the connected one or more ultrasound transducers, based on the acquired information.

13. The ultrasound diagnostic apparatus according to claim 12,
wherein the processor is configured to:
acquire, as the information on the one or more ultrasound transducers, unique information on a model or a machine body of the connected one or more ultrasound transducers; and
select the one or more of the multiple types of correction data stored in the storage, associated with the connected one or more ultrasound transducers based on the unique information.

14. The ultrasound diagnostic apparatus according to claim 1,
wherein the processor is configured to generate the analysis data for an entire scan range of the observation target.

15. The ultrasound diagnostic apparatus according to claim 1,
wherein the processor is configured to generate the analysis data only for a designated region of interest in a scan range of the observation target.

16. The ultrasound diagnostic apparatus according to claim 5,
wherein the processor is configured to set a common depth within a predetermined depth range including a focal depth of at least one spectral data of the first reference data, the second reference data, and the correction data.

17. A method for operating an ultrasound diagnostic apparatus for generating an ultrasound image based on an ultrasound signal acquired by an ultrasound probe having an ultrasound transducer, the ultrasound transducer being configured to transmit an ultrasound wave to an observation target and to receive the ultrasound wave reflected from the observation target, the method comprising:
generating analysis data based on the ultrasound signal received from the observation target; and
correcting the analysis data by using correction data based on first reference data and second reference data, the first reference data being obtained from an ultrasound signal received from a reference reflector by using the ultrasound transducer or another ultrasound transducer of a same model as that of the ultrasound transducer, the second reference data being obtained from the ultrasound signal received from the reference reflector by using a specific ultrasound transducer provided in a standard ultrasound endoscope that is selected for one model and allows sensitivity of the another ultrasound transducer or the ultrasound transducer to be coincident with sensitivity of the specific ultrasound transducer at every frequency.

18. A non-transitory computer-readable recording medium with an executable program stored thereon for operating an ultrasound diagnostic apparatus, the ultrasound diagnostic apparatus being configured to generate an ultrasound image based on an ultrasound signal acquired by an ultrasound probe having an ultrasound transducer, the ultrasound transducer being configured to transmit an ultrasound wave to an observation target and to receive the ultrasound wave reflected from the observation target, the program causing the ultrasound diagnostic apparatus to execute:
generating analysis data based on the ultrasound signal received from the observation target; and
correcting the analysis data by using correction data based on first reference data and second reference data, the first reference data being obtained from an ultrasound signal received from a reference reflector by using the ultrasound transducer or another ultrasound transducer of a same model as that of the ultrasound transducer, the second reference data being obtained from the ultrasound signal received from the reference reflector by using a specific ultrasound transducer provided in a standard ultrasound endoscope that is selected for one model and allows sensitivity of the another ultrasound transducer or the ultrasound transducer to be coincident with sensitivity of the specific ultrasound transducer at every frequency.

\* \* \* \* \*